US012390132B2

(12) United States Patent
Harper

(10) Patent No.: US 12,390,132 B2
(45) Date of Patent: *Aug. 19, 2025

(54) METHODS AND SYSTEMS FOR EARLY SIGNAL ATTENUATION DETECTION AND PROCESSING

(71) Applicant: ABBOTT DIABETES CARE INC., Alameda, CA (US)

(72) Inventor: Wesley Scott Harper, Alameda, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/682,484

(22) Filed: Feb. 28, 2022

(65) Prior Publication Data

US 2022/0287601 A1 Sep. 15, 2022

Related U.S. Application Data

(63) Continuation of application No. 17/411,154, filed on Aug. 25, 2021, now Pat. No. 11,298,056, which is a continuation of application No. 17/245,719, filed on Apr. 30, 2021, now Pat. No. 11,116,431, which is a continuation of application No. 16/228,910, filed on Dec. 21, 2018, now Pat. No. 11,013,431, which is a continuation of application No. 15/061,774, filed on Mar. 4, 2016, now Pat. No. 10,194,844, which is a continuation of application No. 13/925,694, filed on Jun. 24, 2013, now Pat. No. 9,310,230, which is a continuation of application No. 12/769,635, filed on Apr. 28, 2010, now Pat. No. 8,483,967.

(60) Provisional application No. 61/173,600, filed on Apr. 29, 2009.

(51) Int. Cl.
A61B 5/145 (2006.01)
A61B 5/1473 (2006.01)
A61B 5/1495 (2006.01)
G01D 18/00 (2006.01)
G01N 31/22 (2006.01)
G01N 33/66 (2006.01)
G16H 40/40 (2018.01)

(52) U.S. Cl.
CPC ........ *A61B 5/14532* (2013.01); *A61B 5/1473* (2013.01); *A61B 5/1495* (2013.01); *G01D 18/00* (2013.01); *G01N 31/22* (2013.01); *G01N 33/66* (2013.01); *G16H 40/40* (2018.01)

(58) Field of Classification Search
CPC . A61B 5/14532; A61B 5/1473; A61B 5/1495; G16H 40/40; G01D 18/00; G01N 31/22; G01N 33/66
See application file for complete search history.

(56) References Cited

U.S. PATENT DOCUMENTS

| | | | |
|---|---|---|---|
| 3,581,062 A | 5/1971 | Aston |
| 3,926,760 A | 12/1975 | Allen et al. |
| 3,949,388 A | 4/1976 | Fuller |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,425,920 A | 1/1984 | Bourland et al. |
| 4,441,968 A | 4/1984 | Emmer et al. |
| 4,464,170 A | 8/1984 | Clemens et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,759,828 A | 7/1988 | Young et al. |

(Continued)

FOREIGN PATENT DOCUMENTS

EP 0098592 1/1984
EP 0127958 12/1984

(Continued)

OTHER PUBLICATIONS

Armour, J. C., et al., "Application of Chronic Intravascular Blood Glucose Sensor in Dogs", Diabetes, vol. 39, 1990, pp. 1519-1526.

(Continued)

*Primary Examiner* — Jerry Lin
(74) *Attorney, Agent, or Firm* — ONE LLP

(57) ABSTRACT

Provided are methods and apparatus for receiving sensor data from an analyte sensor of a sensor monitoring system, processing the received sensor data with time corresponding calibration data, outputting the processed sensor data, detecting one or more adverse conditions associated with the sensor monitoring system, disabling the output of the sensor data during the adverse condition time period, determining that the one or more detected adverse conditions is no longer present in the sensor monitoring system, retrieving the sensor data during the adverse condition time period, processing the retrieved sensor data during the adverse condition time period, and outputting the processed retrieved sensor data.

28 Claims, 7 Drawing Sheets

(56) References Cited

U.S. PATENT DOCUMENTS

| | | |
|---|---|---|
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,202,261 A | 4/1993 | Musho et al. |
| 5,210,778 A | 5/1993 | Massart |
| 5,228,449 A | 7/1993 | Christ et al. |
| 5,231,988 A | 8/1993 | Wernicke et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,394,877 A | 3/1995 | Orr et al. |
| 5,402,780 A | 4/1995 | Faasse, Jr. |
| 5,408,999 A | 4/1995 | Singh et al. |
| 5,410,326 A | 4/1995 | Goldstein |
| 5,411,647 A | 5/1995 | Johnson et al. |
| 5,431,160 A | 7/1995 | Wilkins |
| 5,431,921 A | 7/1995 | Thombre |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,552,997 A | 9/1996 | Massart |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,640,954 A | 6/1997 | Pfeiffer et al. |
| 5,653,239 A | 8/1997 | Pompei et al. |
| 5,665,222 A | 9/1997 | Heller et al. |
| 5,711,001 A | 1/1998 | Bussan et al. |
| 5,711,861 A | 1/1998 | Ward et al. |
| 5,726,646 A | 3/1998 | Bane et al. |
| 5,735,285 A | 4/1998 | Albert et al. |
| 5,748,103 A | 5/1998 | Flach et al. |
| 5,771,891 A | 6/1998 | Gozani |
| 5,772,586 A | 6/1998 | Heinonen et al. |
| 5,791,344 A | 8/1998 | Schulman et al. |
| 5,807,375 A | 9/1998 | Gross et al. |
| 5,875,186 A | 2/1999 | Belanger et al. |
| 5,899,855 A | 5/1999 | Brown |
| 5,914,026 A | 6/1999 | Blubaugh, Jr. et al. |
| 5,925,021 A | 7/1999 | Castellano et al. |
| 5,942,979 A | 8/1999 | Luppino |
| 5,951,521 A | 9/1999 | Mastrototaro et al. |
| 5,954,643 A | 9/1999 | VanAntwerp et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,987,353 A | 11/1999 | Khatchatrian et al. |
| 5,995,860 A | 11/1999 | Sun et al. |
| 6,001,067 A | 12/1999 | Shults et al. |
| 6,004,278 A | 12/1999 | Botich et al. |
| 6,022,315 A | 2/2000 | Iliff |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,129,823 A | 10/2000 | Hughes et al. |
| 6,134,461 A | 10/2000 | Say et al. |
| 6,141,573 A | 10/2000 | Kurnik et al. |
| 6,143,164 A | 11/2000 | Heller et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,471,689 B1 | 10/2002 | Joseph et al. |
| 6,478,736 B1 | 11/2002 | Mault |
| 6,484,045 B1 | 11/2002 | Holker et al. |
| 6,484,046 B1 | 11/2002 | Say et al. |

(56) References Cited

U.S. PATENT DOCUMENTS

| | | |
|---|---|---|
| 6,493,069 B1 | 12/2002 | Nagashimada et al. |
| 6,498,043 B1 | 12/2002 | Schulman et al. |
| 6,514,718 B2 | 2/2003 | Heller et al. |
| 6,546,268 B1 | 4/2003 | Ishikawa et al. |
| 6,551,494 B1 | 4/2003 | Heller et al. |
| 6,554,798 B1 | 4/2003 | Mann et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,654,625 B1 | 11/2003 | Say et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciurczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,770,030 B1 | 8/2004 | Schaupp et al. |
| 6,789,195 B1 | 9/2004 | Prihoda et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,837,858 B2 | 1/2005 | Cunningham et al. |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,895,265 B2 | 5/2005 | Silver |
| 6,923,763 B1 | 8/2005 | Kovatchev et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,015,817 B2 | 3/2006 | Copley et al. |
| 7,016,713 B2 | 3/2006 | Gardner et al. |
| 7,024,245 B2 | 4/2006 | Lebel et al. |
| 7,025,774 B2 | 4/2006 | Freeman et al. |
| 7,027,848 B2 | 4/2006 | Robinson et al. |
| 7,027,931 B1 | 4/2006 | Jones et al. |
| 7,041,068 B2 | 5/2006 | Freeman et al. |
| 7,041,468 B2 | 5/2006 | Drucker et al. |
| 7,046,153 B2 | 5/2006 | Oja et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,123,950 B2 | 10/2006 | Mannheimer |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,171,274 B2 | 1/2007 | Starkweather et al. |
| 7,179,226 B2 | 2/2007 | Crothall et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,226,442 B2 | 6/2007 | Sheppard et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,299,082 B2 | 11/2007 | Feldman et al. |
| 7,310,544 B2 | 12/2007 | Brister et al. |
| 7,324,012 B2 | 1/2008 | Mann et al. |
| 7,329,239 B2 | 2/2008 | Safabash et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,424,318 B2 | 9/2008 | Brister et al. |
| 7,429,258 B2 | 9/2008 | Angel et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbies et al. |
| 7,651,596 B2 | 1/2010 | Petisce et al. |
| 7,651,845 B2 | 1/2010 | Doyle, III et al. |
| 7,654,956 B2 | 2/2010 | Brister et al. |
| 7,657,297 B2 | 2/2010 | Simpson et al. |
| 7,697,967 B2 | 4/2010 | Stafford |
| 7,699,775 B2 | 4/2010 | Desai et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |

(56) References Cited

U.S. PATENT DOCUMENTS

| | | |
|---|---|---|
| 7,736,310 B2 | 6/2010 | Taub |
| 7,736,344 B2 | 6/2010 | Moberg et al. |
| 7,763,042 B2 | 7/2010 | Iio et al. |
| 7,766,829 B2 | 8/2010 | Sloan et al. |
| 7,811,231 B2 | 10/2010 | Jin et al. |
| 7,813,809 B2 | 10/2010 | Strother et al. |
| 7,822,454 B1 | 10/2010 | Alden et al. |
| 7,889,069 B2 | 2/2011 | Fifolt et al. |
| 7,899,545 B2 | 3/2011 | John |
| 7,914,460 B2 | 3/2011 | Melker et al. |
| 7,938,797 B2 | 5/2011 | Estes |
| 7,941,200 B2 | 5/2011 | Weinert et al. |
| 7,946,985 B2 | 5/2011 | Mastrototaro et al. |
| 7,972,296 B2 | 7/2011 | Braig et al. |
| 7,976,466 B2 | 7/2011 | Ward et al. |
| 7,978,063 B2 | 7/2011 | Baldus et al. |
| 8,010,174 B2 | 8/2011 | Goode, Jr. et al. |
| 8,010,256 B2 | 8/2011 | Oowada |
| 8,192,394 B2 | 6/2012 | Estes et al. |
| 8,282,549 B2 | 10/2012 | Brauker et al. |
| 8,597,570 B2 | 12/2013 | Terashima et al. |
| 8,764,651 B2 | 7/2014 | Tran |
| 8,771,183 B2 | 7/2014 | Sloan |
| 8,864,651 B2 | 10/2014 | Kuyava et al. |
| 9,241,631 B2 | 1/2016 | Valdes et al. |
| 9,504,471 B2 | 11/2016 | Vaitekunas et al. |
| 9,577,934 B2 | 2/2017 | Gross |
| 9,808,574 B2 | 11/2017 | Yodfat et al. |
| 9,996,668 B2 | 6/2018 | Reihman et al. |
| 10,085,640 B2 | 10/2018 | Mensinger et al. |
| 10,820,842 B2 | 11/2020 | Harper |
| 10,827,954 B2 | 11/2020 | Hoss et al. |
| 10,874,338 B2 | 12/2020 | Stafford |
| 10,881,341 B1 | 1/2021 | Curry et al. |
| 10,945,647 B2 | 3/2021 | Mazza et al. |
| 10,945,649 B2 | 3/2021 | Lee et al. |
| 10,952,653 B2 | 3/2021 | Harper |
| 10,959,654 B2 | 3/2021 | Curry et al. |
| 10,966,644 B2 | 4/2021 | Stafford |
| 10,973,443 B2 | 4/2021 | Funderburk et al. |
| 10,980,461 B2 | 4/2021 | Simpson et al. |
| 11,000,213 B2 | 5/2021 | Kamath et al. |
| 11,000,216 B2 | 5/2021 | Curry et al. |
| 11,013,440 B2 | 5/2021 | Lee et al. |
| 11,064,917 B2 | 7/2021 | Simpson et al. |
| 11,116,431 B1 | 9/2021 | Harper |
| 11,141,084 B2 | 10/2021 | Funderburk et al. |
| 11,298,056 B2 | 4/2022 | Harper |
| 2001/0020124 A1 | 9/2001 | Tamada |
| 2001/0037060 A1 | 11/2001 | Thompson et al. |
| 2001/0037366 A1 | 11/2001 | Webb et al. |
| 2001/0047604 A1 | 12/2001 | Valiulis |
| 2002/0019022 A1 | 2/2002 | Dunn et al. |
| 2002/0054320 A1 | 5/2002 | Ogino |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0107557 A1 | 8/2002 | Edell et al. |
| 2002/0111832 A1 | 8/2002 | Judge |
| 2002/0128594 A1 | 9/2002 | Das et al. |
| 2002/0133107 A1 | 9/2002 | Darcey |
| 2002/0147135 A1 | 10/2002 | Schnell |
| 2002/0161288 A1 | 10/2002 | Shin et al. |
| 2002/0188748 A1 | 12/2002 | Blackwell et al. |
| 2003/0004403 A1 | 1/2003 | Drinan et al. |
| 2003/0005464 A1 | 1/2003 | Gropper et al. |
| 2003/0021729 A1 | 1/2003 | Moller et al. |
| 2003/0023461 A1 | 1/2003 | Quintanilla et al. |
| 2003/0028089 A1 | 2/2003 | Galley et al. |
| 2003/0060692 A1 | 3/2003 | Ruchti et al. |
| 2003/0060753 A1 | 3/2003 | Starkweather et al. |
| 2003/0065536 A1 | 4/2003 | Hansen et al. |
| 2003/0114897 A1 | 6/2003 | Von Arx et al. |
| 2003/0147515 A1 | 8/2003 | Kai et al. |
| 2003/0163351 A1 | 8/2003 | Brown |
| 2003/0168338 A1 | 9/2003 | Gao et al. |
| 2003/0199790 A1 | 10/2003 | Boecker et al. |
| 2003/0208113 A1 | 11/2003 | Mault et al. |
| 2003/0212379 A1 | 11/2003 | Bylund et al. |
| 2004/0010207 A1 | 1/2004 | Flaherty et al. |
| 2004/0015102 A1 | 1/2004 | Cummings et al. |
| 2004/0041749 A1 | 3/2004 | Dixon |
| 2004/0054263 A1 | 3/2004 | Moerman et al. |
| 2004/0060818 A1 | 4/2004 | Feldman et al. |
| 2004/0063435 A1 | 4/2004 | Sakamoto et al. |
| 2004/0064068 A1 | 4/2004 | DeNuzzio et al. |
| 2004/0073266 A1 | 4/2004 | Haefner et al. |
| 2004/0078215 A1 | 4/2004 | Dahlin et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135684 A1 | 7/2004 | Steinthal et al. |
| 2004/0138588 A1 | 7/2004 | Saikley et al. |
| 2004/0147872 A1 | 7/2004 | Thompson |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186365 A1 | 9/2004 | Jin et al. |
| 2004/0193025 A1 | 9/2004 | Steil et al. |
| 2004/0204687 A1 | 10/2004 | Mogensen et al. |
| 2004/0204868 A1 | 10/2004 | Maynard et al. |
| 2004/0223985 A1 | 11/2004 | Dunfiled et al. |
| 2004/0247671 A1 | 12/2004 | Prescott et al. |
| 2004/0249253 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004494 A1 | 1/2005 | Perez et al. |
| 2005/0027177 A1 | 2/2005 | Shin et al. |
| 2005/0031689 A1 | 2/2005 | Shults et al. |
| 2005/0038680 A1 | 2/2005 | McMahon |
| 2005/0043598 A1 | 2/2005 | Goode, Jr. et al. |
| 2005/0049179 A1 | 3/2005 | Davidson et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096516 A1 | 5/2005 | Soykan et al. |
| 2005/0113886 A1 | 5/2005 | Fischell et al. |
| 2005/0114068 A1 | 5/2005 | Chey et al. |
| 2005/0116683 A1 | 6/2005 | Cheng et al. |
| 2005/0137530 A1 | 6/2005 | Campbell et al. |
| 2005/0173245 A1 | 8/2005 | Feldman et al. |
| 2005/0176136 A1 | 8/2005 | Burd et al. |
| 2005/0182306 A1 | 8/2005 | Sloan |
| 2005/0184153 A1 | 8/2005 | Auchinleck |
| 2005/0187442 A1 | 8/2005 | Cho et al. |
| 2005/0192493 A1 | 9/2005 | Wuori |
| 2005/0195930 A1 | 9/2005 | Spital et al. |
| 2005/0204134 A1 | 9/2005 | Von Arx et al. |
| 2005/0214892 A1 | 9/2005 | Kovatchev et al. |
| 2005/0245799 A1 | 11/2005 | Brauker et al. |
| 2005/0251033 A1 | 11/2005 | Scarantino et al. |
| 2005/0277912 A1 | 12/2005 | John |
| 2005/0283209 A1 | 12/2005 | Katoozi et al. |
| 2006/0001538 A1 | 1/2006 | Kraft et al. |
| 2006/0001551 A1 | 1/2006 | Kraft et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0017923 A1 | 1/2006 | Ruchti et al. |
| 2006/0020300 A1 | 1/2006 | Nghiem et al. |
| 2006/0031094 A1 | 2/2006 | Cohen et al. |
| 2006/0079740 A1 | 4/2006 | Silver et al. |
| 2006/0091006 A1 | 5/2006 | Wang et al. |
| 2006/0099971 A1 | 5/2006 | Staton et al. |
| 2006/0142651 A1 | 6/2006 | Brister et al. |
| 2006/0154642 A1 | 7/2006 | Scannell |
| 2006/0161225 A1 | 7/2006 | Sormann et al. |
| 2006/0166629 A1 | 7/2006 | Reggiardo |

(56) References Cited

U.S. PATENT DOCUMENTS

| | | |
|---|---|---|
| 2006/0173406 A1 | 8/2006 | Haves et al. |
| 2006/0189863 A1 | 8/2006 | Peyser et al. |
| 2006/0193375 A1 | 8/2006 | Lee et al. |
| 2006/0202859 A1 | 9/2006 | Mastrototaro et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0226985 A1 | 10/2006 | Goodnow et al. |
| 2006/0247508 A1 | 11/2006 | Fennell |
| 2006/0247985 A1 | 11/2006 | Liamos et al. |
| 2006/0258929 A1 | 11/2006 | Goode et al. |
| 2006/0272652 A1 | 12/2006 | Stocker et al. |
| 2006/0290496 A1 | 12/2006 | Peeters et al. |
| 2006/0293607 A1 | 12/2006 | Alt et al. |
| 2007/0010950 A1 | 1/2007 | Abensour et al. |
| 2007/0016381 A1 | 1/2007 | Karnath et al. |
| 2007/0017983 A1 | 1/2007 | Frank et al. |
| 2007/0027381 A1 | 2/2007 | Stafford |
| 2007/0033074 A1 | 2/2007 | Nitzan et al. |
| 2007/0060869 A1 | 3/2007 | Tolle et al. |
| 2007/0060979 A1 | 3/2007 | Strother et al. |
| 2007/0066956 A1 | 3/2007 | Finkel |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078818 A1 | 4/2007 | Zvitz et al. |
| 2007/0093786 A1 | 4/2007 | Goldsmith et al. |
| 2007/0118030 A1 | 5/2007 | Bruce et al. |
| 2007/0149875 A1 | 6/2007 | Ouyang et al. |
| 2007/0173706 A1 | 7/2007 | Neinast et al. |
| 2007/0173708 A9 | 7/2007 | Dobbies et al. |
| 2007/0173709 A1 | 7/2007 | Petisce et al. |
| 2007/0173710 A1 | 7/2007 | Petisce et al. |
| 2007/0191702 A1 | 8/2007 | Yodfat et al. |
| 2007/0203407 A1 | 8/2007 | Hoss et al. |
| 2007/0203539 A1 | 8/2007 | Stone et al. |
| 2007/0203966 A1 | 8/2007 | Brauker et al. |
| 2007/0208246 A1 | 9/2007 | Brauker et al. |
| 2007/0228071 A1 | 10/2007 | Kamen et al. |
| 2007/0231846 A1 | 10/2007 | Cosentino et al. |
| 2007/0232878 A1 | 10/2007 | Kovatchev et al. |
| 2007/0235331 A1 | 10/2007 | Simpson et al. |
| 2007/0249922 A1 | 10/2007 | Peyser et al. |
| 2007/0255116 A1 | 11/2007 | Mehta et al. |
| 2007/0255321 A1 | 11/2007 | Gerber et al. |
| 2007/0255348 A1 | 11/2007 | Holtzclaw |
| 2008/0004904 A1 | 1/2008 | Tran |
| 2008/0009692 A1 | 1/2008 | Stafford |
| 2008/0033254 A1 | 2/2008 | Karnath et al. |
| 2008/0039702 A1 | 2/2008 | Hayter et al. |
| 2008/0045824 A1 | 2/2008 | Tapsak et al. |
| 2008/0060955 A1 | 3/2008 | Goodnow |
| 2008/0061961 A1 | 3/2008 | John |
| 2008/0081977 A1 | 4/2008 | Hayter et al. |
| 2008/0083617 A1 | 4/2008 | Simpson et al. |
| 2008/0092638 A1 | 4/2008 | Brenneman et al. |
| 2008/0114228 A1 | 5/2008 | McCluskey et al. |
| 2008/0119705 A1 | 5/2008 | Patel et al. |
| 2008/0125636 A1 | 5/2008 | Ward et al. |
| 2008/0127052 A1 | 5/2008 | Stoker |
| 2008/0161666 A1 | 7/2008 | Feldman et al. |
| 2008/0172205 A1 | 7/2008 | Breton et al. |
| 2008/0177149 A1 | 7/2008 | Weinert et al. |
| 2008/0194934 A1 | 8/2008 | Ray et al. |
| 2008/0194938 A1 | 8/2008 | Brister et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0214900 A1 | 9/2008 | Fennell et al. |
| 2008/0214918 A1 | 9/2008 | Brister et al. |
| 2008/0228045 A1 | 9/2008 | Gao et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234943 A1 | 9/2008 | Ray et al. |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0262469 A1 | 10/2008 | Brister et al. |
| 2008/0269714 A1 | 10/2008 | Mastrototaro et al. |
| 2008/0269723 A1 | 10/2008 | Mastrototaro et al. |
| 2008/0287764 A1 | 11/2008 | Rasdal et al. |
| 2008/0296155 A1 | 12/2008 | Shults et al. |
| 2008/0300572 A1 | 12/2008 | Rankers et al. |
| 2008/0306434 A1 | 12/2008 | Dobbies et al. |
| 2008/0306435 A1 | 12/2008 | Karnath et al. |
| 2008/0306444 A1 | 12/2008 | Brister et al. |
| 2008/0312841 A1 | 12/2008 | Hayter |
| 2008/0312859 A1 | 12/2008 | Skyggebjerg et al. |
| 2008/0319085 A1 | 12/2008 | Wright et al. |
| 2009/0006061 A1 | 1/2009 | Thukral et al. |
| 2009/0012377 A1 | 1/2009 | Jennewine et al. |
| 2009/0018424 A1 | 1/2009 | Karnath et al. |
| 2009/0024177 A1 | 1/2009 | Shuros et al. |
| 2009/0030294 A1 | 1/2009 | Petisce et al. |
| 2009/0033482 A1 | 2/2009 | Hayter et al. |
| 2009/0036758 A1 | 2/2009 | Brauker et al. |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0048503 A1 | 2/2009 | Dalal et al. |
| 2009/0054747 A1 | 2/2009 | Fennell |
| 2009/0054748 A1 | 2/2009 | Feldman |
| 2009/0054749 A1 | 2/2009 | He |
| 2009/0055149 A1 | 2/2009 | Hayter et al. |
| 2009/0062633 A1 | 3/2009 | Brauker et al. |
| 2009/0076356 A1 | 3/2009 | Simpson et al. |
| 2009/0076360 A1 | 3/2009 | Brister et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088787 A1 | 4/2009 | Koike et al. |
| 2009/0093687 A1 | 4/2009 | Telfort et al. |
| 2009/0099436 A1 | 4/2009 | Brister et al. |
| 2009/0105636 A1 | 4/2009 | Hayter et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0156924 A1 | 6/2009 | Shariati et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Karnath et al. |
| 2009/0192751 A1 | 7/2009 | Karnath et al. |
| 2009/0198118 A1 | 8/2009 | Hayter et al. |
| 2009/0216100 A1 | 8/2009 | Ebner et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Karnath et al. |
| 2009/0242425 A1 | 10/2009 | Karnath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |

(56) References Cited

U.S. PATENT DOCUMENTS

| | | |
|---|---|---|
| 2009/0299276 A1 | 12/2009 | Brauker et al. |
| 2010/0076283 A1 | 3/2010 | Simpson et al. |
| 2010/0093786 A1 | 4/2010 | Watanabe et al. |
| 2010/0096259 A1 | 4/2010 | Zhang et al. |
| 2010/0105999 A1 | 4/2010 | Dixon et al. |
| 2010/0113897 A1 | 5/2010 | Brenneman et al. |
| 2010/0141656 A1 | 6/2010 | Krieftewirth |
| 2010/0145377 A1 | 6/2010 | Lai et al. |
| 2010/0146300 A1 | 6/2010 | Brown |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168540 A1 | 7/2010 | Karnath et al. |
| 2010/0168541 A1 | 7/2010 | Karnath et al. |
| 2010/0168542 A1 | 7/2010 | Karnath et al. |
| 2010/0168543 A1 | 7/2010 | Karnath et al. |
| 2010/0168544 A1 | 7/2010 | Karnath et al. |
| 2010/0168545 A1 | 7/2010 | Karnath et al. |
| 2010/0168546 A1 | 7/2010 | Karnath et al. |
| 2010/0168657 A1 | 7/2010 | Karnath et al. |
| 2010/0174168 A1 | 7/2010 | Goode, Jr. et al. |
| 2010/0174266 A1 | 7/2010 | Estes |
| 2010/0179399 A1 | 7/2010 | Goode, Jr. et al. |
| 2010/0179402 A1 | 7/2010 | Goode, Jr. et al. |
| 2010/0179405 A1 | 7/2010 | Goode, Jr. et al. |
| 2010/0179408 A1 | 7/2010 | Karnath et al. |
| 2010/0179409 A1 | 7/2010 | Karnath et al. |
| 2010/0185065 A1 | 7/2010 | Goode, Jr. et al. |
| 2010/0185071 A1 | 7/2010 | Simpson et al. |
| 2010/0185072 A1 | 7/2010 | Goode, Jr. et al. |
| 2010/0185073 A1 | 7/2010 | Goode, Jr. et al. |
| 2010/0185074 A1 | 7/2010 | Goode, Jr. et al. |
| 2010/0185075 A1 | 7/2010 | Brister et al. |
| 2010/0185175 A1 | 7/2010 | Kamen et al. |
| 2010/0198034 A1 | 8/2010 | Thomas et al. |
| 2010/0198035 A1 | 8/2010 | Karnath et al. |
| 2010/0198142 A1 | 8/2010 | Sloan et al. |
| 2010/0213057 A1 | 8/2010 | Feldman et al. |
| 2010/0213080 A1 | 8/2010 | Celentano et al. |
| 2010/0217105 A1 | 8/2010 | Yodfat et al. |
| 2010/0262201 A1 | 10/2010 | He et al. |
| 2010/0313105 A1 | 12/2010 | Nekoomaram et al. |
| 2010/0331642 A1 | 12/2010 | Bruce et al. |
| 2011/0002223 A1 | 1/2011 | Gross |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0077490 A1 | 3/2011 | Simpson et al. |
| 2011/0148905 A1 | 6/2011 | Simmons et al. |
| 2011/0178461 A1 | 7/2011 | Chong et al. |
| 2011/0208027 A1 | 8/2011 | Wagner et al. |
| 2011/0257895 A1 | 10/2011 | Brauker et al. |
| 2011/0287528 A1 | 11/2011 | Fern et al. |
| 2011/0320130 A1 | 12/2011 | Valdes et al. |
| 2012/0078071 A1 | 3/2012 | Bohm et al. |
| 2012/0108931 A1 | 5/2012 | Taub et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2013/0035575 A1 | 2/2013 | Mayou et al. |
| 2013/0127627 A1 | 5/2013 | Hayter et al. |
| 2013/0235166 A1 | 9/2013 | Jones et al. |
| 2014/0176338 A1 | 6/2014 | He et al. |
| 2017/0112531 A1 | 4/2017 | Schoonmaker et al. |
| 2019/0216373 A1 | 7/2019 | Harper |

FOREIGN PATENT DOCUMENTS

| | | |
|---|---|---|
| EP | 0320109 | 6/1989 |
| EP | 0390390 | 10/1990 |
| EP | 0396788 | 11/1990 |
| EP | 1 707 115 A2 | 10/2006 |
| WO | WO-00/59370 | 10/2000 |
| WO | WO 00/62664 A1 | 10/2000 |
| WO | WO-01/52935 | 7/2001 |
| WO | WO-01/54753 | 8/2001 |
| WO | WO-03/82091 | 10/2003 |
| WO | WO-2008/001366 | 1/2008 |
| WO | WO 2008/051409 A2 | 5/2008 |
| WO | WO 2008/052199 A3 | 5/2008 |
| WO | WO 2008/061552 A1 | 5/2008 |
| WO | WO 2009/005952 A2 | 1/2009 |

OTHER PUBLICATIONS

Bennion, N., et al., "Alternate Site Glucose Testing: A Crossover Design", Diabetes Technology & Therapeutics. vol. 4, No. 1, 2002, pp. 25-33.

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.

Brooks, S. L., et al., "Development of an On-line Glucose Sensor for Fermentation Monitoring", Biosensors, vol. 3, 1987, pp. 45-56.

Cass, A. E.G., et al., "Ferrocene-Medicated Enzyme Electrode for Amperometric Determination of Glucose", Analytical Chemistry, vol. 56, No. 4, 1984, pp. 667-671.

Cheyne, E.H., et al., "Performance of a Continuous Glucose Monitoring System During Controlled Hypoglycaemia in Healthy Volunteers", Diabetes Technology & Therapeutics, vol. 4, No. 5, 2002, pp. 607-613.

Csoregi, E., et al., "Design and Optimization of a Selective Subcutaneously Implantable Glucose Electrode Based on "Wired" Glucose Oxidase", Analytical Chemistry, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5 No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.

Isermann, R., "Supervision, Fault-Detection and Fault-Diagnosis Methods—An Introduction", Control Engineering Practice, vol. 5, No. 5, 1997, pp. 639-652.

Isermann, R., et al., "Trends in the Application of Model-Based Fault Detection and Diagnosis of Technical Processes", Control Engineering Practice, vol. 5, No. 5, 1997, pp. 709-719.

Johnson, P. C., "Peripheral Circulation", John Wiley & Sons, 1978, p. 198.

Jovanovic, L., "The Role of Continuous Glucose Monitoring in Gestational Diabetes Mellitus", Diabetes Technology & Therapeutics, vol. 2, Suppl. 1, 2000, pp. S67-S71.

Jungheim, K., et al., "How Rapid Does Glucose Concentration Change in Daily Life of Patients With Type 1 Diabetes?", Diabetologia, vol. 45, 2002, pp. 250.

Jungheim, K., et al., "Risky Delay of Hypoglycemia Detection by Glucose Monitoring at the Arm", Diabetes Care, vol. 24, No. 7, 2001, pp. 1303-1304.

Kaplan, S. M., "Wiley Electrical and Electronics Engineering Dictionary", IEEE Press, 2004, pp. 141, 142, 548, 549.

Lodwig, V., et al., "Continuous Glucose Monitoring with Glucose Sensors: Calibration and Assessment Criteria", Diabetes Technology & Therapeutics, vol. 5, No. 4, 2003, pp. 573-587.

Lortz, J., et al., "What is Bluetooth? We Explain the Newest Short-Range Connectivity Technology", Smart Computing Learning Series, Wireless Computing, vol. 8, Issue 5, 2002, pp. 72-74.

Malin, S. F., et al., "Noninvasive Prediction of Glucose by Near-Infrared Diffuse Reflectance Spectroscopy", Clinical Chemistry, vol. 45, No. 9, 1999, pp. 1651-1658.

(56) References Cited

OTHER PUBLICATIONS

McGarraugh, G., et al., "Glucose Measurements Using Blood Extracted from the Forearm and the Finger", TheraSense, Inc., 2001, 16 Pages.
McGarraugh, G., et al., "Physiological Influences on Off-Finger Glucose Testing", Diabetes Technology & Therapeutics, vol. 3, No. 3, 2001, pp. 367-376.
McKean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.
Morbiducci, U., et al., "Improved usability of the minimal model of insulin sensitivity based on an automated approach and genetic algorithms for parameter estimation", Clinical Science, vol. 112, 2007, pp. 257-263.
Mougiakakou, S.G., et al., "A Real Time Simulation Model of Glucose-Insulin Metabolism for Type 1 Diabetes Patients", Proceedings of the 2005 IEEE Engineering in Medicine and Biology $27^{th}$ Annual Conference, 2005, pp. 298-301.
Parker, R., et al., "Robust $H_\infty$ Glucose Control in Diabetes Using a Physiological Model", AIChE Journal, vol. 46, No. 12, 2000, pp. 2537-2549.
Pickup, J. C., et al., "Implantable Glucose Sensors: Choosing the Appropriate Sensing Strategy", Biosensors, vol. 3, 1987/88, pp. 335-346.
Pickup, J. C., et al., "In vivo molecular sensing in diabetes mellitus: an implantable glucose sensor with direct electron transfer", Diabetologia, vol. 32, 1989, pp. 213-217.
Pishko, M. V., et al., "Amperometric Glucose Microelectrodes Prepared t hrough Immobilization of Glucose Oxidase in Redox Hydrogels", Analytical Chemistry, vol. 63, No. 20, 1991, pp. 2268-2272.
Quinn, C. P., et al., "Kinetics of glucose delivery to subcutaneous tissue in rats measured with 0.3-mm amperometric microsensors", American Journal of Physiology, vol. 269, No. 1, 1995, E155-E161.
Roe, J. N., et al., "Bloodless Glucose Measurements", Critical Reviews™ in Therapeutic Drug Carrier Systems, vol. 15, Issue 3, 1998, pp. 199-241.
Sakakida, M., et al., "Development of ferrocene-mediated needle-type glucose sensor as a measure of true subcutaneous tissue glucose concentrations", Artificial Organs Today, vol. 2, No. 2, 1992, pp. 145-158.
Sakakida, M., et al., "Ferrocene-mediated needle-type glucose sensor covered with newly designed biocompatible membrane", Sensors and Actuators B, vol. 13-14, 1993, pp. 319-322.
Salehi, C., et al., "A Telemetry-Instrumentation System for Long-Term Implantable Glucose and Oxygen Sensors", Analytical Letters, vol. 29, No. 13, 1996, pp. 2289-2308.
Schmidtke, D. W., et al., "Measurement and modeling of the transient difference between blood and subcutaneous glucose concentrations in the rat after injection of insulin", Proceedings of the National Academy of Sciences, vol. 95, 1998, pp. 294-299.
Shaw, G. W., et al., "In Vitro testing of a simply constructed, highly s table glucose s ensor suitable for i mplantation in d iabetic p atients", Biosensors & Bioelectronics, vol. 6, 1991, pp. 401-406.
Shichiri, M., et al., "Glycaemic Control in Pancreatectomized Dogs with a Wearable Artificial Endocrine Pancreas", Diabetologia, vol. 24, 1983, pp. 179-184.
Shichiri, M., et al., "In Vivo Characteristics of Needle-Type Glucose Sensor-Measurements of Subcutaneous Glucose Concentrations in Human Volunteers", Hormone and Metabolic Research Supplement Series, vol. 20, 1988, pp. 17-20.
Shichiri, M., et al., "Membrane design for extending the l ong-life of an implantable g lucose sensor", Diabetes Nutrition and Metabolism, vol. 2, 1989, pp. 309-313.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.
Shichiri, M., et al., "Wearable Artificial Endocrine Pancreas With Needle-Type Glucose Sensor", The Lancet, 1982, pp. 1129-1131.
Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.
Sternberg, R., et al., "Study and Development of Multilayer Needle-type Enzyme-based Glucose Microsensors", Biosensors, vol. 4, 1988, pp. 27-40.
Thompson, M., et al., "In Vivo Probes: Problems and Perspectives", Clinical Biochemistry, vol. 19, 1986, pp. 255-261.
Turner, A.P.F., et al., "Diabetes Mellitus: Biosensors for Research and Management", Biosensors, vol. 1, 1985, pp. 85-115.
Updike, S. J., et al., "Principles of Long-term Fully Implanted Sensors with Emphasis on Radiotelemetric Monitoring of Blood Glucose from i nside a Subcutaneous Foreign Body Capsule (FBC)", Biosensors in the Body: Continuous In vivo Monitoring, Chapter 4, 1997, pp. 117-137.
Velho, G., et al., "Strategies for calibrating a subcutaneous glucose sensor", Biomedica Biochimica Acta, vol. 48, 1989, pp. 957-964.
Wilson, G. S., et al., "Progress toward the Development of an Implantable Sensor for Glucose", Clinical Chemistry, vol. 38, No. 9, 1992, pp. 1613-1617.
US, Exhibit 653-1 from DexCom, Inc.'s Preliminary Invalidity Contentions, Case No. 21-CV-977-KAJ (D. Delaware), May 6, 2022.
US, Exhibit 653-2 from DexCom, Inc.'s Preliminary Invalidity Contentions, Case No. 21-CV-977-KAJ (D. Delaware), May 6, 2022.
US, Exhibit 653-3 from DexCom, Inc.'s Preliminary Invalidity Contentions, Case No. 21-CV-977-KAJ (D. Delaware), May 6, 2022.
US, Exhibit 653-4 from DexCom, Inc.'s Preliminary Invalidity Contentions, Case No. 21-CV-977-KAJ (D. Delaware), May 6, 2022.
US, Exhibit 653-5 from DexCom, Inc.'s Preliminary Invalidity Contentions, Case No. 21-CV-977-KAJ (D. Delaware), May 6, 2022.
US, Exhibit 842-1 from DexCom, Inc.'s Preliminary Invalidity Contentions, Case No. 21-CV-977-KAJ (D. Delaware), May 6, 2022.
US, Exhibit 842-2 from DexCom, Inc.'s Preliminary Invalidity Contentions, Case No. 21-CV-977-KAJ (D. Delaware), May 6, 2022.
US, Exhibit 842-3 from DexCom, Inc.'s Preliminary Invalidity Contentions, Case No. 21-CV-977-KAJ (D. Delaware), May 6, 2022.
US, Exhibit 842-4 from DexCom, Inc.'s Preliminary Invalidity Contentions, Case No. 21-CV-977-KAJ (D. Delaware), May 6, 2022.
US, Exhibit 842-5 from DexCom, Inc.'s Preliminary Invalidity Contentions, Case No. 21-CV-977-KAJ (D. Delaware), May 6, 2022.
US, Defendant Dexcom, Inc.'s Corrected First Supplemental Response to Plaintiffs' Interrogatories 3 and 4, Case 21-CV-977-KAJ (D. Delaware), Mar. 31, 2022.
US, Dexcom, Inc.'s Answer to First Amended Complaint and Affirmative Defenses to Plaintiffs' First Amended Complaint, Case 21-CV-977-KAJ (D. Delaware), Feb. 22, 2022.
US, Transcript of Oral Arguments, Case 21-CV-977-KAJ (D. Delaware), Feb. 11, 2022.
US, Order Denying Dexcom, Inc.'s Motion to Dismiss, Case 21-CV-977-KAJ (D. Delaware), Feb. 8, 2022.
US, Defendant Dexcom, Inc.'s Response to Plaintiffs First Set of Interrogatories, Case 21-CV-977-KAJ (D. Delaware), Dec. 10, 2021.
US, Defendant Dexcom, Inc.'s Reply Brief in Support of its Motion to Dismiss Pursuant to Federal Rule of Civil Procedure 12(b)(6), Case 21-CV-977-KAJ (D. Delaware), Nov. 22, 2021.

(56) References Cited

OTHER PUBLICATIONS

US, Plaintiffs Answering Brief in Opposition to Defendant Motion to Dismiss Under Rule 12(b)(6), Case 21-CV-977-KAJ (D. Delaware), Nov. 15, 2021.
US, Defendant Dexcom, Inc.'s Appendix to Opening Brief in Support of its Motion to Dismiss Pursuant to Federal Rule of Civil Procedure 12(b)(6), Case 21-CV-977-KAJ (D. Delaware), Nov. 1, 2021.
US, Defendant Dexcom, Inc.'s Opening Brief in Support of its Motion to Dismiss Pursuant to Federal Rule of Civil Procedure 12(b)(6), Case 21-CV-977-KAJ (D. Delaware), Nov. 1, 2021.
US, Defendant Dexcom, Inc.'s Motion to Dismiss Under Rule 12(b)(6), Case 21-CV-977-KAJ (D. Delaware), Nov. 1, 2021.
US, First Amended Complaint filed by Abbott Diabetes Care Inc. and Abbott Diabetes Care Limited against Dexcom, Inc., Case 21-CV-977-KAJ (D. Delaware), Oct. 4, 2021.
US, Complaint filed by Abbott Diabetes Care Inc. and Abbott Diabetes Care Limited against Dexcom, Inc., Case 21-CV-977-KAJ (D. Delaware), Jul. 1, 2021.
Graff, T., et al., "Ocean Systems Test and Evaluation Program—Data Communications Plan", National Oceanic and Atmospheric Administration, 2006, pp. 1-199.
Guardian® RT Continuous Glucose Monitoring System REF MMT-7900 User Guide, 2005, pp. 1-128.
Medtronic Guardian® REAL-Time Continuous Glucose Monitoring System User Guide, 2006, pp. 1-181.
US, Exhibit 653-1S from DexCom, Inc.'s First Supplemental Preliminary Invalidity Contentions, Case No. 21-CV-977-KAJ (D. Delaware), May 6, 2022.
US, Exhibit 653-4S from DexCom, Inc.'s First Supplemental Preliminary Invalidity Contentions, Case No. 21-CV-977-KAJ (D. Delaware), May 6, 2022.
US, Exhibit 653-5S from DexCom, Inc.'s First Supplemental Preliminary Invalidity Contentions, Case No. 21-CV-977-KAJ (D. Delaware), May 6, 2022.
US, Exhibit 653-6 from DexCom, Inc.'s Preliminary Invalidity Contentions, Case No. 21-CV-977-KAJ (D. Delaware), May 6, 2022.
US, Exhibit 842-1S from DexCom, Inc.'s First Supplemental Preliminary Invalidity Contentions, Case No. 21-CV-977-KAJ (D. Delaware), May 6, 2022.
US, Exhibit 842-4S from DexCom, Inc.'s First Supplemental Preliminary Invalidity Contentions, Case No. 21-CV-977-KAJ (D. Delaware), May 6, 2022.
US, Exhibit 842-5S from DexCom, Inc.'s First Supplemental Preliminary Invalidity Contentions, Case No. 21-CV-977-KAJ (D. Delaware), May 6, 2022.
US, Exhibit 842-6 from DexCom, Inc.'s Preliminary Invalidity Contentions, Case No. 21-CV-977-KAJ (D. Delaware), May 6, 2022.
US, Defendant Dexcom, Inc.'s First Supplemental Preliminary Invalidity Contentions, Case No. 21-CV-977-KAJ (D. Delaware), May 6, 2022.
US, Defendant Dexcom, Inc.'s Preliminary Invalidity Contentions, Case No. 21-CV-977-KAJ (D. Delaware), May 6, 2022.
Exhibit 842-6F from DexCom, Inc.'s Final Invalidity Contentions, Case No. 21-CV-977-KAJ (D. Delaware), Feb. 9, 2023.
Exhibit 842-5F from DexCom, Inc.'s Final Invalidity Contentions, Case No. 21-CV-977-KAJ (D. Delaware), Feb. 9, 2023.
Exhibit 842-3F from DexCom, Inc.'s Final Invalidity Contentions, Case No. 21-CV-977-KAJ (D. Delaware), Feb. 9, 2023.
Exhibit 842-2F from DexCom, Inc.'s Final Invalidity Contentions, Case No. 21-CV-977-KAJ (D. Delaware), Feb. 9, 2023.
Exhibit 842-1F from DexCom, Inc.'s Final Invalidity Contentions, Case No. 21-CV-977-KAJ (D. Delaware), Feb. 9, 2023.
Exhibit 653-6F from DexCom, Inc.'s Final Invalidity Contentions, Case No. 21-CV-977-KAJ (D. Delaware), Feb. 9, 2023.
Exhibit 653-5F from DexCom, Inc.'s Final Invalidity Contentions, Case No. 21-CV-977-KAJ (D. Delaware), Feb. 9, 2023.
Exhibit 653-3F from DexCom, Inc.'s Final Invalidity Contentions, Case No. 21-CV-977-KAJ (D. Delaware), Feb. 9, 2023.
Exhibit 653-2F from DexCom, Inc.'s Final Invalidity Contentions, Case No. 21-CV-977-KAJ (D. Delaware), Feb. 9, 2023.
Exhibit 653-1F from DexCom, Inc.'s Final Invalidity Contentions, Case No. 21-CV-977-KAJ (D. Delaware), Feb. 9, 2023.
Defendant Dexcom, Inc's Objections and Responses to Plaintiffs' Second Set of Interrogatories, Case 21-CV-977-KAJ (D. Delaware), Oct. 11, 2022.
Defendant Dexcom, Inc's Second Supplemental Preliminary Invalidity Contentions, Oct. 4, 2022.
Defendant's Comments on Plaintiffs' Technology Tutorial, Case 21-CV-977-KAJ (D. Delaware)—Redacted Version, Sep. 16, 2022.
Plaintiffs' Response to Defendant's Third Set of Interrogatories, Nos. 12-15, Case 21-CV-977-KAJ (D. Delaware), Sep. 14, 2022.
Plaintiffs' Comments on Defendant's Technology Tutorial, Case 21-CV-977-KAJ (D. Delaware), Sep. 9, 2022.
Plaintiffs' Second Supplemental Response to Defendant's First Set of Interrogatories, Nos. 1-10, Interrogatory No. 5, Case 21-CV-977-KAJ (D. Delaware), Sep. 8, 2022.
Plaintiffs' First Updated Identification of Asserted Claims, Case 21-CV-977-KAJ (D. Delaware), Sep. 7, 2022.
Second Declaration of John D. Villasenor, PH.D, Case 21-CV-977-KAJ (D. Delaware), Aug. 31, 2022.
Defendant's Sur-Reply Claim Construction Brief, Case 21-CV-977-KAJ (D. Delaware), Aug. 31, 2022.
Expert Declaration of Majid Sarrafzadeh, Ph.D., in Support of Abbott's Reply Claim Construction Brief, Case 21-CV-977-KAJ (D. Delaware), Aug. 17, 2022.
Plaintiffs' Reply Brief Regarding Claim Construction, Case 21-CV-977-KAJ (D. Delaware), Aug. 17, 2022.
Plaintiff's Response to Defendant's Second Set of Interrogatories, No. 11, Case 21-CV-977-KAJ (D. Delaware) of John D. Villasenor, PH.D, Case 21-CV-977-KAJ (D. Delaware), Aug. 8, 2022.
Declaration of John D. Villasenor, PH.D, Case 21-CV-977-KAJ (D. Delaware), Aug. 3, 2022.
Defendant's Answering Claim Construction Brief, Case 21-CV-977-KAJ (D. Delaware), Aug. 3, 2022.
Expert Declaration of Majid Sarrafzadeh, Ph.D., in Support of Abbott's Opening Claim Construction Brief, Case 21-CV-977-KAJ (D. Delaware), Jul. 13, 2022.
Plaintiffs' Opening Claim Construction Brief, Case 21-CV-977-KAJ (D. Delaware), Jul. 13, 2022.
Dexcom, Inc.'s Answer to Second Amended Complaint, Case 21-CV-977-KAJ (D. Delaware), Jun. 30, 2022.
Joint Claim Construction Chart, Case 21-CV-977-KAJ (D. Delaware), Jun. 22, 2022.
Plaintiffs' Second Amended Complaint, Case 21-CV-977-KAJ (D. Delaware), May 20, 2022.
Defendant Dexcom, Inc.'s Supplemental Response to Plaintiff's First Set of Interrogatories, No. 4, Case 21-CV-977-KAJ (D. Delaware), May 9, 2022.
Dexcom, Inc.'s Amended Answer to Second Amended Complaint, Case No. 21-CV-977-KAJ (D. Delaware)—Public Version, Mar. 17, 2023.
Complaint, Case No. 23-CV-239-UNA (D. Delaware), Mar. 3, 2023.
Exhibit 842-7F from DexCom, Inc.'s Final Invalidity Contentions, Case No. 21-CV-977-KAJ (D. Delaware), Feb. 3, 2023.
Exhibit 842-4F from DexCom, Inc.'s Final Invalidity Contentions, Case No. 21-CV-977-KAJ (D. Delaware), Feb. 3, 2023.
Exhibit 653-4F from DexCom, Inc.'s Final Invalidity Contentions, Case No. 21-CV-977-KAJ (D. Delaware), Feb. 3, 2023.
Defendant Dexcom, Inc's Supplemental Objections and Responses to Plaintiffs' Second Set of Interrogatories, Nos. 11, 14, 15, 21-25 [Corrected], Case 21-CV-977-KAJ (D. Delaware), Dec. 20, 2022.
"Abbott Receives CE Mark for Freestyle® Libre, A Revolutionary Glucose Monitoring System for People With Diabetes", 2014, 7 pages.
"Alcove", Webster's New College Dictionary, 2001, p. 26.
Armstrong, S., "Wireless connectivity for health and sports monitoring: a review", Br J Sports Med, 2007, vol. 41, pp. 285-289.

(56) References Cited

OTHER PUBLICATIONS

Boise, M., "Dexcom CEO Kevin Sayer Explains G6", 2018, retrieved from https://beyondtype1.org/dexcom-ceo-kevin-sayer-explains-g6/, 9 pages.

Breton, M, D., et al., "Optimum Subcutaneous Glucose Sampling and Fourier Analysis of Continuous Glucose Monitors", Journal of Diabetes Science and Technology, 2008, vol. 2, No. 3, pp. 495-500.

Buckingham, B., et al., "Real-time continuous glucose monitoring", Curr Opin Endocrinol Diabetes Obes, 2007, vol. 14, pp. 288-295.

Buckingham, B., "Clinical Overview of Continuous Glucose Monitoring", Journal of Diabetes Science and Technology, 2008, vol. 2, No. 2, pp. 300-306.

Burge, M.R., et al., "Continuous Glucose Monitoring: The Future of Diabetes Management", Diabetes Spectrum, 2008, vol. 21, No. 2, pp. 112-119.

Certified True Copy of Preliminary Amendment filed on Apr. 20, 2018 for U.S. Pat. No. 10,827,954, 7 pages.

CGMs Changing Diabetes Management: Kevin Sayer, DIC Interview Transcript, 2019, retrieved from https://www.diabetesincontrol.com/cgms-changing-diabetes-management-kevin-sayer-dic-interview-transcript/, 10 pages.

Choleau, C., et al., "Calibration of a Subcutaneous Amperometric Glucose Sensor Implanted for 7 Days in Diabetic Patients Part 2. Superiority of the One-Point Calibration Method", Biosensor & Bioelectronics, 2002, vol. 17, No. 8, pp. 647-654.

"Deciding When to Submit a 510(k) for a Change to an Existing Device, Guidance for Industry and Food and Drug Administration Staff", 2017, pp. 1-77.

"Deciding When to Submit a 510(k) for a Software Change to an Existing Device, Guidance for Industry and Food and Drug Administration Staff", 2017, pp. 1-31.

Dexcom CEO- Prime Position in Our Market—Mad Money—CNBC.mp4, Transcript 2023 by Sonix, 2 pages.

DexCom (DXCM) 2017 Q4 Earnings Call Transcript, 2017, retrieved from https://docoh.com/transcript/1093557/2017Q4/DXCM, 11 pages.

DexCom (DCXM) Q1 2018 Results - Earnings Call Transcript, 2018, retrieved from https://seekingalpha.com/article/4168949-dexcom-dxcm-q1-2018-results-earnings-call-transcript, 4 pages.

Dexcom, Inc. NasdaqGS:DXCM Company Conference Presentation, 2019, 10 pages.

Dexcom, Inc. NasdaqGS:DXCM Company Conference Presentation, 2020, 9 pages.

Dexcom, Inc. NasdaqGS:DXCM Company Conference Presentation, 2021, 16 pages.

Dexcom G6 Continuous Glucose Monitoring System User Guide, 2019, pp. 1-27.

Dexcom G6 Start Here Set up Guide, 2019, pp. 1-8.

Dexcom G6 Using Your G6 Guide, Mar. 2020, pp. 1-7.

"Does Dexcom Really Have a Future If It Can't Match Abbott's Scale", 2019, retrieved from https://www.sprucepointcap.com/reports/dxcm_research_thesis_3-21-2019.pdf, p. 46.

Email chain from Sophie Hood, oldest email dated Jan. 24, 2023, 5 pages.

"FDA authorizes first fully interoperable continuous glucose monitoring system, streamlines review pathway for similar devices", FDA News Release, 2018, retrieved from https://www.fda.gov/news-events/press-announcements/fda-authorizes-first-fully-interoperable-continuous-glucose-monitoring-system-streamlines-review, 3 pages.

Frequently Asked Questions About the MiniMed Paradigm® REAL-Time System, 2007, 12 pages.

FreeStyle Navigator Continuous Glucose Monitoring System FDA Premarket Approval (PMA), 2008, pp. 1-7.

Heller, A., et al., "Electrochemical Glucose Sensors and Their Applications in Diabetes Management", Chemical Reviews, 2008, vol. 108, No. 7, pp. 2482-2505.

Hoss, U., et al., "Continuous Glucose Monitoring in Subcutaneous Tissue Using Factory-Calibrated Sensors: A Pilot Study", Diabetes Technology & Therapeutics, 2010, vol. 12, No. 8, pp. 591-597.

Hoss, U., et al., "Feasibility of Factory Calibration for Subcutaneous Glucose Sensors in Subjects With Diabetes", Journal of Diabetes Science and Technology, 2014, vol. 8, No. 1, pp. 89-94.

"Housing", "recess", "release", and "retain", Merriam-Webster's Collegiate Dictionary, Tenth Edition, 1999, pp. 563, 975, 987, and 999.

"Housing" and "recess", The New Penguin English Dictionary, 2000, pp. 678 and 1167.

IEEE 100 The Authoritative Dictionary of IEEE Standards Terms, Seventh Edition, 2000, 3 pages.

"An Interview with Kevin Sayer, President and CEO of Dexcom, About The New G6", 2021, 5 pages.

Keenan, D. B., et al., "Delays in Minimally Invasive Continuous Glucose Monitoring Devices: A Review of Current Technology", Journal of Diabetes Science and Technology, 2009, vol. 3, No. 5, pp. 1207-1214.

Mastrototaro, J. J., "The MiniMed Continuous Glucose Monitoring System", Diabetes Technology & Therapeutics, 2000, vol. 2, Suppl. 1, pp. S13 - S-18.

Mcgarraugh, G., "The Chemistry of Commercial Continuous Glucose Monitors", Diabetes Technology & Therapeutics, 2009, vol. 11, Suppl. 1, pp. S17 - S-24.

Medtronic MiniMed Paradigm® REAL-Time Insulin Pump and Continuous Glucose Monitoring System, 2007, 6 pages.

Medtronic MiniMed Paradigm® REAL-Time 522 and 722 Sensor Features User Guide, 2006, pp. 1-68.

Medtronic MiniMed Paradigm® REAL-Time System Features, 2007, 6 pages.

Medtronic MiniMed Paradigm® REAL-Time System Frequently Asked Questions, 2007, 6 pages.

Medtronic MiniMed Paradigm® REAL-Time System Fact Sheet, 2007, 6 pages.

Medtronic MiniMed Paradigm® REAL-Time System Premarket Approval (PMA), 2006, pp. 1-3.

Medtronic MiniMed Paradigm® REAL-Time System User Guides, 2007, 2 pages.

Medtronic MiniMed Paradigm® REAL-Time 522 and 722 Insulin Pumps User Guide, 2008, pp. 1-262.

"Medtronic Receives FDA Approval for World's First Insulin Pump with Real-Time Continuous Glucose Monitoring", News Release, 2006, 2 pages.

Omnipod image, Exhibit 182 of ADC Reply Brief SJ, Daubert, Sep. 22, 2022, 2 pages.

Order, Federal Communications Commission, 2006, pp. 1-8.

Pantelopoulos, A., et al., "A Survey on Wearable Biosensor Systems for Health Monitoring", 30th Annual International IEEE Embs Conference, 2008, British Columbia, Canada, pp. 4887-4890.

Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", Diabetologia, 1993, vol. 36, pp. 658-663.

Program, 2nd International Conference on Advanced Technologies & Treatments for Diabetes, Athens, Greece, 2009, 3 pages.

"Recess", Cambridge Dictionary of American English, 2000, pp. 710-711.

"Retract", The Chambers Dictionary, 1998, p. 1410.

"Retract", The New Oxford American Dictionary, 2001, p. 1455.

"Retract", Webster's Third New International Dictionary, 1993, pp. 1939-1940.

Roberts, S. S., Mail Call and "The Diabetes Advisor", Diabetes Forecast, 2007, vol. 60, No. 12, pp. 10, 13, 15, 94, 96, 98, and 100.

Ruder, K., "Continuous Glucose Monitors For Kids", Diabetes Forecast, 2007, 1 page.

Shenoi, B, A., Introduction to Digital Signal Processing and Filter Design, 2006, Chapter 1, Introduction, pp. 1-31.

Smith, S. W., The Scientist and Engineer's Guide to Digital Signal Processing, Second Edition, 1997-1999, Chapter 28, Digital Signal Processors, pp. 503-534.

Tegnestedt, C., et al., "Levels and sources of sound in the intensive care unit—an observational study of three room types", Acta Anaesthiesiologica Scandinavica, 2013, pp. 1-10.

(56) References Cited

OTHER PUBLICATIONS

Velho, G., et al., "In vivo calibration of a subcutaneous glucose sensor for determination of subcutaneous glucose kinetics", Diab. Nutr. Metab., 1988, vol. 3, pp. 227-233.
Watkin, J., "An Introduction to Flash Glucose Monitoring", 14 pages.
14708172.3 Communication of the Board of Appeal.
Notice of Filing Date Accorded to Petition and Time for Filing Patent Owner Preliminary Response, IPR No. 2023-01252.
Petitioner's Explanation of Material Differences Between Petitions, IPR Nos. 2023-01251 and 2023-01252.
Petition For Inter Partes Review Of U.S. Pat. No. 11,298,056, IPR No. 2023-01252.
Declaration of Morten O. Jensen, Ph.D., Dr. Med, IPR No. 2023-01252.
Notice of Filing Date Accorded to Petition and Time for Filing Patent Owner Preliminary Response, IPR No. 2023-01251.
Petition For Inter Partes Review Of U.S. Pat. No. 11,298,056, IPR No. 2023-01251.
Declaration of Brian D. Gross, IPR No. 2023-01251.
Petitioner's Reply to Patent Owner's Response to Petition, IPR No. 2022-00605.
Supplemental Declaration of Gary D. Fletcher, Ph.D, IPR No. 2022-00605.
Declaration of Gary D. Fletcher, Ph.D, pp. 75-77, IPR No. 2022-00605.
Petition For Inter Partes Review Of U.S. Pat. No. 10,945,649, IPR No. 2022-00605.
Exhibit 3P to the Proposed Pretrial Order Abbott's Statement of Issues of Law Which Remain to be Litigated, Case No. 21-CV-977-KAJ (D. Delaware).
Exhibit 3D to the Proposed Pretrial Order Dexcom's Statement of Issues of Law Which Remain to be Litigated, Case No. 21-CV-977-KAJ (D. Delaware).
Exhibit 2P to the Proposed Pretrial Order Abbott's Statement of Issue of Fact Which Remain to be Litigated, Case No. 21-CV-977-KAJ (D. Delaware).
Exhibit 2D to Proposed Pretrial Order Dexcom's Statement of Contested Facts, Case No. 21-CV-977-KAJ (D. Delaware).
Exhibit 1 to the Proposed Pretrial Order Parties Joint Statement of Uncontroverted Facts, Case No. 21-CV-977-KAJ (D. Delaware).
Amended [Proposed] Final Pretrial Order, Case No. 21-CV-977-KAJ (D. Delaware).
Memorandum Opinion, Case No. 21-CV-977-KAJ (D. Delaware)—Public Version.
Order, Case No. 21-CV-977-KAJ (D. Delaware).
Appendix of Attachments and Exhibits for Plaintiffs' Opening Letter Brief in Support of Plaintiffs' Motion to Strike Defendant's New Claim Constructions, Case No. 21-CV-977-KAJ (D. Delaware)—Public Version.
Opening Letter Brief in Support of Plaintiffs' Motion to Strike Defendant's New Claim Constructions, Case No. 21-CV-977-KAJ (D. Delaware)—Public Version.
Dexcom's Letter Brief in Opposition to Abbott's Motion to Strike, Case No. 21-CV-977-KAJ (D. Delaware)—Public Version.
Plaintiffs' Motion to Strike Defendant's New Claim Constructions, Case No. 21-CV-977-KAJ (D. Delaware).
Transcript of Motion Hearing, Case No. 21-CV-977-KAJ (D. Delaware).
Defendant Dexcom, Inc.'s Reply Brief in Support of its Motion to Strike Abbott's Late-Disclosed Supplemental Declarations, Case No. 21-CV-977-KAJ (D. Delaware)—Public Version.
Appendix of Exhibits in Support of Dexcom, Inc.'s Opposition to Plaintiffs' Motion for Summary Judgement and Daubert Challenges—vol. 2, Case No. 21-CV-977-KAJ (D. Delaware)—Public Version.
Appendix of Exhibits in Support of Dexcom, Inc.'s Opposition to Plaintiffs' Motion for Summary Judgement and Daubert Challenges—vol. 1, Case No. 21-CV- 977-KAJ (D. Delaware)—Public Version.
Defendant Dexcom, Inc.'s Appendix to Brief in Support of its Reply to Abbott Diabetes Care Inc. and Abbott Diabetes Care Limited's Opposition to Dexcom Inc.'s Motions for Summary Judgement, Case No. 21-CV-977-Kaj (D. Delaware)—Public Version.
Appendix of Exhibits and Attachments for Plaintiffs' Responsive Letter Brief In Opposition to Dexcom's Motion to Strike Expert Declarations (D.I. 408), Case No. 21-CV-977-KAJ (D. Delaware)—Public Version.
Plaintiffs' Responsive Letter Brief in Opposition to Defendant's Motion to Strike Expert Declarations, Case No. 21-CV-977-KAJ (D. Delaware)—Public Version.
Defendant Dexcom, Inc.'s Appendix to Brief in Support of its Reply to Abbott Diabetes Care Inc. and Abbott Diabetes Care Limited's Opposition to Dexcom Inc.'s Motions to Exclude Expert Reports and Testimony, Case No. 21-CV-977-KAJ (D. Delaware)—Public Version.
Defendant Dexcom, Inc.'s Opening Brief in Support of its Motion to Strike Abbott's Late-Disclosed Supplemental Declarations, Case No. 21-CV-977-KAJ (D. Delaware)—Public Version.
Defendant Dexcom, Inc.'s Reply in Support of Its Motions to Exclude Expert Reports and Testimony, Case No. 21-CV-977-KAJ (D. Delaware)—Public Version.
Dexcom, Inc.'s Motion to Strike Plaintiffs' Untimely Expert Opinions, Case No. 21-CV-977-KAJ (D. Delaware).
Declaration of John L. Smith, PH.D., on Validity, in Support of Plaintiffs' Answering Brief in Opposition to Dexcom's Motions for Summary Judgement and Plaintiffs' Answering Brief in Opposition to Dexcom's Motions to Exclude Expert Reports and Testimony, Case No. 21-CV-977-KAJ (D. Delaware)—Public Version.
Declaration of John L. Smith, PH.D., Regarding Infringement, in Support of Plaintiffs' Answering Brief in Opposition to Dexcom's Motions for Summary Judgement and Plaintiffs' Answering Brief in Opposition to Dexcom's Motions to Exclude Expert Reports and Testimony, Case No. 21-CV-977-KAJ (D. Delaware)—Public Version, Jun. 7, 2023.
Appendix of Exhibits (vol. 3 of 3, Exhibits 151-171) for Plaintiffs' Answering Briefs In Opposition to Dexcom's Motions for Summary Judgement (D.I. 331) and to Exclude Expert Reports and Testimony (D.I. 337), Case No. 21-CV-977-KAJ (D. Delaware)—Public Version, Jun. 7, 2023.
Appendix of Exhibits (vol. 2 of 3, Exhibits 138-150) for Plaintiffs' Answering Briefs In Opposition to Dexcom's Motions for Summary Judgement (D.I. 331) and to Exclude Expert Reports and Testimony (D.I. 337), Case No. 21-CV-977-KAJ (D. Delaware)—Public Version, Jun. 7, 2023.
Appendix of Exhibits (vol. 1 of 3, Exhibits 98-137) for Plaintiffs' Answering Briefs In Opposition to Dexcom's Motions for Summary Judgement (D.I. 331) and to Exclude Expert Reports and Testimony (D.I. 337), Case No. 21-CV-977-KAJ (D. Delaware)—Public Version, Jun. 7, 2023.
Plaintiffs' Answering Brief In Opposition to Dexcom's Motions to Exclude Expert Reports and Testimony, Case No. 21-CV-977-KAJ (D. Delaware)—Public Version, Jun. 7, 2023.
Declaration of Dr. John E. Anderson in Opposition to Defendant Dexcom, Inc.'s Motions to Exclude Expert Reports and Testimony, Case No. 21-CV-977-KAJ (D. Delaware)—Public Version, Jun. 7, 2023.
Declaration of Dr. Eden M. Miller in Opposition to Defendant Dexcom, Inc.'s Motions to Exclude Expert Reports and Testimony, Case No. 21-CV-977-KAJ (D. Delaware)—Public Version, Jun. 7, 2023.
Declaration of Eric B. Hanson in Support of Dexcom's Opposition to Plaintiffs' Motion for Summary Judgement and Daubert Challenges, Case No. 21-CV-977-KAJ (D. Delaware)—Public Version, Jun. 7, 2023.
Declaration of John Mastrototaro, Ph.D. in Support of Dexcom's Motion for Summary Judgement, Case No. 21- CV-977-KAJ (D. Delaware), May 19, 2023.
Defendant Dexcom, Inc.'s Opening Brief in Support of Its Motions to Exclude Expert Reports and Testimony, Case No. 21-CV-977-KAJ (D. Delaware)—Public Version, May 19, 2023.
Video-Recorded Deposition of Neil Sheehan, Ph.D, vol. I (pp. 1 to 221), Case No. 21-CV-977-KAJ (D. Delaware), May 4, 2023.
Video Deposition of Karl R. Leinsing, MSME, PE, vol. I, Case No. 21-CV-977-KAJ (D. Delaware), May 3, 2023.

(56) References Cited

OTHER PUBLICATIONS

Videotaped Deposition of John Mastrototaro, Ph.D, Case No. 21-CV-977-KAJ (D. Delaware), Apr. 26, 2023.
Video-Recorded Deposition of John Smith, Ph.D, Case No. 21-CV-977-KAJ (D. Delaware), Apr. 21, 2023.
Expert Report of John L. Smith, Ph.D., on Infringement of the Asserted Claims of U.S. Pat. No. 10,827,954, Case No. 21-CV-977-KAJ (D. Delaware), Mar. 14, 2023.
Oral Argument Hearing Before Hon. Kent A. Jordan, U.S. Circuit Court Judge, Case No. 21-CV-977-KAJ (D. Delaware), Mar. 9, 2023.
Defendant Dexcom, Inc.'s Supplemental Responses to Plaintiffs Abbott Diabetes Care Inc's. and Abbott Diabetes Care Limited's Notice of Rule 30(b)(6) Deposition, Case No. 21-CV-977-KAJ (D. Delaware), Feb. 8, 2023.
Telephone Conference Before Kent A. Jordan, U.S. Circuit Court Judge, Case No. 21-CV-977-KAJ (D. Delaware) Letter to the Honorable Kent A. Jordan Regarding Discovery Disputes, Case No. 21-CV-977-KAJ (D. Delaware), Jan. 3, 2023.
Defendant Dexcom, Inc.'s Notice of Deposition to Plaintiff Abbott Diabetes Care Limited, Case No. 21-CV-977-KAJ (D. Delaware), Aug. 19, 2022.
Defendant Dexcom, Inc.'s Notice of Deposition to Plaintiff Abbott Diabetes Care Inc., Case No. 21-CV-977-KAJ (D. Delaware, Aug. 19, 2022.
Plaintiffs' Proposed Claim Constructions, Case 21-CV-977-KAJ, May 27, 2022.
Plaintiffs' Identification of Claim Terms For Construction, Case 21-CV-977-KAJ (D. Delaware), May 13, 2022.
Joint Claim Construction Brief, Case 20-1679-RGA-JLH (D. Delaware), Feb. 11, 2022.
Plaintiff Dexcom, Inc.'s Amended Preliminary Disclosure of Asserted Claims and Infringement Contentions to Abbott Diabetes Care Inc. and Abbott Diabetes Care Sales Corp., Case 21-CV-690-ADA ((D. Texas), Jan. 5, 2022.
Order Denying Evenflo's Motion for Summary Judgement of Non-Infringement and Granting in Part and Denying in Part Wonderland's Motion for Partial Summary Judgement, Case 20-CV-727-JPM (D. Delaware), Dec. 6, 2022.
Findings of Fact and Conclusions of Law Regrading Subject Matter Eligibility of U.S. Pat. No. 6,975,308 Under 35 U.S.C. §101, Case 20-CV-101-ADA (D. Texas), Dec. 7, 2021.
Non-Final Office Action issued in U.S. Appl. No. 17/030,030, Dec. 17, 2020, Dec. 17, 2020.
Notice of Allowance issued in U.S. Appl. No. 15/963,828, Mar. 3, 2021.
Response to Non-Final Office Action filed in U.S. Appl. No. 15/963,828, Dec. 8, 2020.
Request Under 37 CRR 1.48(a) to Correct Inventorship filed in U.S. Appl. No. 15/963,828, Dec. 8, 2020.
Joint Declaration Under 37 C.F.R. 1.131 filed in Appl. U.S. Appl. No. 15/963,828, Nov. 30, 2020.
Non-Final Office Action issued in U.S. Appl. No. 14/884,622, Jun. 13, 2018.
Response to Restriction Requirement, and Acknowledgement Receipt, filed in U.S. Appl. No. 14/884,622, Apr. 5, 2018.
Email from John Shaw of Shaw & Keller dated May 16, 2023, 2 pages.
Notice of Filing Date Accorded to Petition and Time for Filing Patent Owner Preliminary Response, IPR No. 2024-00521, Feb. 29, 2024.
Petition for Inter Partes Review of U.S. Pat. No. 11,298,056, IPR No. 2024-00521, Feb. 9, 2024.
Decision Denying Institution of Inter Partes Review 35 U.S.C. § 314, IPR No. 2023-01252, Feb. 5, 2024.
Patent Owner's Response to Petitioner's Explanation of Material Differences Between Petitions, IPR Nos. 2023-01251 and 2023-01252, Jan. 18, 2024.
Patent Owner's Preliminary Response, IPR No. 2023-01252, Nov. 10, 2023.
Declaration of Brian D. Gross, IPR No. 2023-01252, Jul. 24, 2023.
Decision Granting Institution of Inter Partes Review 35 U.S.C. § 314, IPR No. 2023-01251, Feb. 5, 2024.
Patent Owner's Response to Petitioner's Explanation of Material Differences Between Petitions, IPR Nos. 2023-01251 and 2023-01252, Nov. 10, 2023.
Patent Owner's Preliminary Response, IPR No. 2023-01251, Nov. 10, 2023.
Petitioner's Explanation of Material Differences Between Petitions, IPR No. 2023-01251 and 2023-01252, Apr. 12, 2022.
Joint Letter to the Honorable Kent A. Jordan Regarding Additional Issues Related to the Upcoming Trial, Case No. 21-CV-977-KAJ (D. Delaware), Oct. 6, 2023.
[Joint Proposed] Verdict Form, Case No. 21-CV-977-KAJ (D. Delaware), Oct. 4, 2023.
Memorandum Opinion, Case No. 21-CV-977-KAJ (D. Delaware), Mar. 22, 2023.
Bluetooth Basics, 2006, retrieved from https://web.archive.org/web/20060611161103/http://www.bluetooth.com/Bluetooth/Learn/Basics/, 1 page.
Declaration of Nathaniel E. Frank-White, Nov. 9, 2023, 28 pages.
Dexcom G4 Platinum Pediatric Continuous Glucose Monitoring System User's Guide, 2015, pp. 1-234.
Dexcom G5 Mobile Continuous Glucose Monitoring System FDA Premarket Approval (PMA), 2016, pp. 1-4.
Dexcom STS®-7 Continuous Glucose Monitoring System User's Guide, 2007, pp. 1-74.
"Discover Dexcom G5 Mobile Continuous Glucose Monitoring (CGM) System", 2023, retrieved from https://www.dexcom.com/en-AE/g5-mobile-ae-english, 18 pages.
Explore The Monroe Street Market Community, retrieved from https://www.monroestreetmarket.com/floor-plans/apartment/B-231 on May 10, 2023, 2 pages.
Fcc Online Table of Frequency Allocations, Federal Communications Commission Office of Engineering and Technology Policy and Rules Division, 2022, 180 pages.
"FDA Approves Dexcom G5® Mobile Continuous Glucose Monitoring System", 2015, retrieved from https://www.dexcom.com/news/1257506247-fda-approves-dexcom-g5®- mobile-continuous-glucose-monitoring-system, 6 pages.
Hoss, U., et al., "Continuous glucose monitoring in the tissue: Do we really need to calibrate in-vivo?", Feb. 28, 2009, pp. 1-21.
IPhone User Guide For IOS 8.4 Software, 2015, 196 pages.
Medtronic CareLink™ Personal, Getting Started, 2007, 20 pages.
Scheduling Order, IPR No. 2023-01251, Feb. 5, 2024.
Patent Owner's Sur-Reply in Support of the Patent Owner Preliminary Response, IPR No. 2023-01251, Dec. 18, 2023.
Petitioner's Reply to Patent Owner's Preliminary Response, IPR No. 2023-01251, Dec. 7, 2023.
[Proposed] Final Pretrial Order, vol. 3, Case No. 21-CV-977-KAJ (D. Delaware), Jan. 12, 2024.
[Proposed] Final Pretrial Order, vol. 2, Case No. 21-CV-977-KAJ (D. Delaware), Jan. 12, 2024.
Exhibit 7P to the Proposed Pretrial Order Abbott's Brief Summary of Opinion Testimony, Case No. 21-CV-977-KAJ (D. Delaware), Jan. 4, 2024.
Exhibit 7D to the Proposed Pretrial Order Dexcom's Brief Summary of Opinion Testimony, Case No. 21-CV-977-KAJ (D. Delaware), Jan. 4, 2024.
Exhibit 6P to the Proposed Pretrial Order Abbott's Deposition Designations, Case No. 21-CV-977-KAJ (D. Delaware), Jan. 4, 2024.
Exhibit 6D to the Proposed Pretrial Order Dexcom's Deposition Designations, Case No. 21-CV-977-KAJ (D. Delaware), Jan. 4, 2024.
Exhibit 5P to the Proposed Pretrial Order Abbott's List of Trial Exhibits, Case No. 21-CV-977-KAJ (D. Delaware), Jan. 4, 2024.
Exhibit 5D to the Proposed Pretrial Order Dexcom's List of Trial Exhibits, Case No. 21-CV-977-KAJ (D. Delaware), Jan. 4, 2024.
Exhibit 4 to the Proposed Pretrial Order Joint List of Trial Exhibits, Case No. 21-CV-977-KAJ (D. Delaware), Jan. 4, 2024.

(56) References Cited

OTHER PUBLICATIONS

Exhibit 3P to the Proposed Pretrial Order Abbott's Statement of Issues of Law Which Remain to be Litigated, Case No. 21-CV-977-KAJ (D. Delaware), Jan. 4, 2024.
Exhibit 3D to the Proposed Pretrial Order Dexcom's Statement of Issues of Law Which Remain to be Litigated, Case No. 21-CV-977-KAJ (D. Delaware), Jan. 4, 2024.
Exhibit 2P to the Proposed Pretrial Order Abbott's Statement of Issues of Fact Which Remain to be Litigated, Case No. 21-CV-977-KAJ (D. Delaware), Jan. 4, 2024.
Exhibit 2D to the Proposed Pretrial Order Dexcom's Statement of Contested Facts, Case No. 21-CV-977-KAJ (D. Delaware), Jan. 4, 2024.
Exhibit 1 to the Proposed Pretrial Order Parties' Joint Statement of Uncontroverted Facts, Case No. 21-CV- 977-KAJ (D. Delaware), Jan. 4, 2024.
[Proposed] Final Pretrial Order, Case No. 21-CV-977-KAJ (D. Delaware), Jan. 4, 2024.
Video Deposition of Laura B. Stamm, vol. 1, Case No. 21-CV-977-KAJ (D. Delaware), Apr. 28, 2023.
Telephonic Proceedings, Case No. 21-CV-977-KAJ (D. Delaware), Apr. 5, 2023.
Report of Karl R. Leinsing, MSME, PE, Regarding Infringement of U.S. Pat. Nos. 10,973,443, 11,000,216, 10,881,341, 10,959,654, 10,945,649, and 11,013,440, Case No. 21-CV-977-KAJ (D. Delaware), Mar. 14, 2023.
Defendant Dexcom, Inc.'s Supplemental Responses and Objections to Plaintiffs Abbott Diabetes Care Inc.'s and Abbott Diabetes Care Limited's Notice of Rule 30(b)(6) Deposition, Case No. 21-CV-977-KAJ (D. Delaware), Feb. 28, 2023.
Plaintiff's Second Set of Interrogatories (Nos. 10-33) to Defendant, Case No. 21-CV-977-KAJ (D. Delaware), Sep. 8, 2022.
Plaintiff's First Set of Interrogatories (Nos. 1-9) to Defendant, Case No. 21-CV-977-KAJ (D. Delaware), Nov. 10, 2021.
List of Challenged Claims, IPR No. 2024-00521, Feb. 9, 2024.
Declaration of Brian D. Gross, IPR No. 2024-00521, Feb. 9, 2024.
Petitioner's Request for Refund of the Post-Institution Fee, IPR No. 2023-01252, Feb. 21, 2024.
Notice of Stipulation, IPR No. 2023-01251, Mar. 22, 2024.
Declaration of Arie Pellikaan, IPR No. 2023-01251, Mar. 5, 2024.
Patent Owner's Objections to Admissibility of Evidence Served with Petition, IPR No. 2023-01251, Feb. 20, 2024.
Petitioner's Updated Mandatory Notices Pursuant to 37 C.F.R. § 42.8(a)(3), IPR No. 2023-01251, Feb. 19, 2024.
Abbott's Initial Claim Charts, Case No. 23-239-KAJ (D. Delaware), Dec. 20, 2023.
Scheduling Order, Case No. 23-239-KAJ (D. Delaware), Sep. 19, 2023.
[Joint Proposed] Final Jury Instructions, Case No. 21-CV-977-KAJ (D. Delaware), Mar. 17, 2024.
[Joint Proposed] Final Jury Instructions, Case No. 21-CV-977-KAJ (D. Delaware), Mar. 7, 2024.
Exhibit 7P to the Proposed Pretrial Order Abbott's Brief Summary of Opinion Testimony, Case No. 21-CV-977-KAJ (D. Delaware), Mar. 7, 2024.
Exhibit 7D to the Proposed Pretrial Order Dexcom's Brief Summary of Opinion Testimony, Case No. 21-CV-977-KAJ (D. Delaware), Mar. 7, 2024.
Exhibit 6P to the Proposed Pretrial Order Abbott's Deposition Designation, Case No. 21-CV-977-KAJ (D. Delaware), Mar. 7, 2024.
Exhibit 6D to the Proposed Pretrial Order Dexcom's Deposition Designation, Case No. 21-CV-977-KAJ (D. Delaware), Mar. 7, 2024.
Exhibit 5P to the Proposed Pretrial Order Abbott's List of Trial Exhibits, Case No. 21-CV-977-KAJ (D. Delaware), Mar. 7, 2024.
Exhibit 5D to the Proposed Pretrial Order Dexcom's List of Trial Exhibits, Case No. 21-CV-977-KAJ (D. Delaware), Mar. 7, 2024.
Exhibit 3P to the Proposed Pretrial Order Abbott's Statement of Issues of Law which Remain to be Litigated, Case No. 21-CV-977-KAJ (D. Delaware), Mar. 7, 2024.
Exhibit 3D to the Proposed Pretrial Order Dexcom's Statement of Issues of Law which Remain to be Litigated, Case No. 21-CV-977-KAJ (D. Delaware), Mar. 7, 2024.
Exhibit 2P to the Proposed Pretrial Order Abbott's Statement of Issues of Fact which Remain to be Litigated, Case No. 21-CV-977-KAJ (D. Delaware), Mar. 7, 2024.
Exhibit 2D to the Proposed Pretrial Order Dexcom's Statement of Contested Facts, Case No. 21-CV-977-KAJ (D. Delaware), Mar. 7, 2024.
Exhibit 1 to the Proposed Pretrial Order Parties' Joint Statement of Uncontroverted Facts, Case No. 21-CV-977-KAJ (D. Delaware), Mar. 7, 2024.
[Proposed] Final Pretrial Order, Case No. 21-CV-977-KAJ (D. Delaware), Mar. 7, 2024.
Joint Stipulation and [Proposed] Order Regarding Dismissal of Certain Asserted Patent Claims, Case No. 21-CV-977-KAJ (D. Delaware), Mar. 1, 2024.
Letter to the Honorable Kent A. Jordan from Nathan R. Hoeschen Regarding Pretrial Order, Redacted, Public Version, Case No. 21-CV-977-KAJ (D. Delaware), Feb. 15, 2024.
Defendant Dexcom, Inc.'s Notice Pursuant to 35 U.S.C. § 282, Case No. 21-CV-977-KAJ (D. Delaware), Feb. 9, 2024.
Letter to Kent A. Jordan, Case No. 21-CV-977-KAJ (D. Delaware), , Feb. 2, 2024.
[Joint Proposed] Final Jury Instructions, Case No. 21-CV-977-KAJ (D. Delaware), Jan. 31, 2024.
Affidavit of Nathaniel E. Frank-White, May 18, 2023, 108 pages.
Affadavit of Nathaniel E Frank-White dated Aug. 16, 2024, 31 pages.
Almurashi, A. M., et al., "Emerging Diabetes Technologies: Continuous Glucose Monitors/Artificial Pancreases", J. Indian Inst. Sci., 2023, pp. 1-26.
American Diabetes Association Standards of Medical Care in Diabetes, Diabetes Care, 2005, vol. 28, Suppl. 1, pp. S4-S36.
American Diabetes Association Standards of Medical Care in Diabetes—2006, Diabetes Care, 2006, vol. 29, Suppl. 1, pp. S4-S41.
American Diabetes Association Standards of Medical Care in Diabetes—2007, Diabetes Care, 2007, vol. 30, Suppl. 1, pp. S4-S42.
Atmel® ATmega169P Datasheet, 2010, 395 pages.
Atmel® Products Selector Guide, 2008, 90 pages.
Bergenstal, R. M., et al., "Effectiveness of Sensor-Augmented Insulin-Pump Therapy in Type 1 Diabetes", The New England Journal of Medicine, 2010, vol. 363, No. 4, pp. 311-320.
Bluetooth Specification, Health Device Profile, 2008, pp. 1-44.
Cappon, G., et al., "Continuous Glucose Monitoring Sensors for Diabetes Management: A Review of Technologies and Applications", Diabetes & Metabolism Journal, 2019, vol. 43, pp. 383-397.
Cather, D. E., "CGM Frustrations Survey", 2020, 36 pages.
Das, S. D., et al., "Review—Electrochemistry and Other Emerging Technologies for Continuous Glucose Monitoring Devices", ECS Sensors Plus, 2022, 19 pages.
Dawson, D. M., "The Integration of Ground-based Real-time Telemetry Processing, On-board Chapter 10 Aircraft Data Recorders, and 802.11G Links", International Telemetering Conference Proceedings, 2005, retrieved from http://hdl.handle.net/10150/604914, 4 pages.
Design Concepts Project Status Update, Glucose Sensor Applicator Dexcom (project #2554), 2014, 5 pages.
Dexcom G5 Mobile System User Guide, 2016, pp. 1-371.
Dexcom G6 Continuous Glucose Monitoring (CGM) System Section 510(k) Approval, 2022, 7 pages.
Dexcom G6 Continuous Glucose Monitoring System User Guide, 2022, pp. 1-341.
Dexcom Seven® Plus Continuous Glucose Monitoring System User's Guide, 2011, pp. 1-144.
Dexcom™ STSTM-7 Continuous Glucose Monitoring System FCC Submission, 2006, 3 pages.
Email from Christopher M Dougherty dated Dec. 17, 2019, 68 pages.
FreeStyle Libre 2 HCP Pulse Report, 2021, 13 pages.

(56) References Cited

OTHER PUBLICATIONS

FreeStyle Libre 3 User's Manual, 2022-2023, pp. iv-241.
Freestyle Navigator User's Guide, 2008, pp. 1-195.
Garg, S., et al., "Flash Glucose Monitoring: The Future Is Here", Diabetes Technology & Therapeutics, 2017, vol. 19, Suppl 2, pp. S-1-S-3.
Grace, R., et al., Vehicle Network Concept Demonstration », International Telemetering Conference Proceedings, 2005, retrieved from http://hdl.handle.net/10150/604790, 10 pages.
Hirsch, I. B., et al., "Role of Continuous Glucose Monitoring in Diabetes Treatment", American Diabetes Association, 2018, p. 1.24.
Hodack, D., "Implementing Inet and the Operational Issues Involved", International Telemetering Conference Proceedings, 2008, retrieved from http://hdl.handle.net/10150/606171, 7 pages.
International Diabetes Device 2022 Blue Book, Seagrove Partners, 142 pages.
Johnson, D. A., et al., Electrochemical Methods for Neuroscience, Chapter 20, Telemetry for Biosensor Systems, 2007, 13 pages.
The Juvenile Diabetes Research Foundation Continuous Glucose Monitoring Study Group, "Continuous Glucose Monitoring and Intensive Treatment of Type 1 Diabetes", The New England Journal of Medicine, 2008, vol. 359, No. 14, pp. 1464-1476.
Mastrototaro, J., et al., "Accuracy of Real-Time Continuous Glucose Monitoring in the Mini-Med Paradigm System," Diabetes, 2007, vol. 56, Suppl. 1, p. A112.
Mathis, M., et al., "TCP Selective Acknowledgement Options", Network Working Group, 1996, 12 pages.
Medtronic Carelink® Personal Quick Start Guide, 2015, 2 pages.
Medtronic MiniMed Guardian Rt Fda Premarket Approval (PMA), 2005, pp. 1-6.
Medtronic MiniMed Guardian RT Summary of Safety and Effectiveness Data, 2005, 13 pages.
Medtronic MiniMed Paradigm® REAL-Time Insulin Pump User Guide, 2007, pp. 1-164.
National Diabetes Statistics Report, Centers for Disease Control and Prevention, 2023, retrieved from https://www.cdc.gov/diabetes/data/statistics-report/index.html, 15 pages.
Sohraby, K., et al., Wireless Sensor Networks: Technology, Protocols, and Application, 2007, pp. xi-306.
Wolpert, H., "Establishing a Continuous Glucose Monitoring Program", Journal of Diabetes Science and Technology, 2008, vol. 2, No. 2, pp. 307-310.
Wright, Jr., E., et al., "Ambulatory Glucose Profiling", The Journal of Family Practice, 2015, vol. 64. No. 12, Supplement, pp. 544-547.
ZigBee Specification, 2007, pp. i-576.
14805745.8 Notice of Opposition, Jul. 26, 2021.
Decision Granting Institution of Inter Partes Review, IPR No. 2024-00521, Aug. 22, 2024.
Patent Owner's Objections To Admissibility of Evidence Served With Petition, IPR No. 2024-00521, Sep. 6, 2024.
Patent Owner's Preliminary Response, IPR No. 2024-00521, May 29, 2024.
Termination, IPR No. 2023-01251, Jan. 8, 2025.
Joint Motion To Terminate Proceeding, IPR No. 2023-01251, Jan. 6, 2025.
Record of Oral Hearing, Paper #39, IPR No. 2023-01251, Nov. 25, 2024.
Record of Oral Hearing, Paper 38, IPR No. 2023-01251, Nov. 25, 2024.
Petitioner Dexcom's Demonstratives, IPR No. 2023-01251, Nov. 4, 2024.
Patent Owner's Demonstratives, IPR No. 2023-01251, Oct. 30, 2024.
Patent Owner's Updated Exhibit List, IPR No. 2023-01251, Oct. 30, 2024.
Patent Owner's Surreply to Petitioner's Reply, IPR No. 2023-01251, Oct. 21, 2024.
Deposition of Andrew Ahmann, MD, IPR No. 2023-01251, Oct. 11, 2024.
Deposition of Brian D. Gross, IPR No. 2023-01251, Oct. 10, 2024.
Declaration of Arie Pellikaan, IPR No. 2023-01251, Sep. 27, 2024.
Patent Owner's Objections to Admissibility of Evidence Served With Petitioner's Reply to Patent Owner's Response, IPR No. 2023-01251, Sep. 13, 2024.
Reply Declaration of Brian D. Gross, IPR No. 2023-01251, Sep. 6, 2024.
Petitioner's Reply to Patent Owner's Response, IPR No. 2023-01251, Sep. 6, 2024.
Deposition of Eugene E. Wright, IPR No. 2023-01251, Jul. 25, 2024.
Deposition of Aaron Striegel, Ph.D, IPR No. 2023-01251, Jul. 24, 2024.
Declaration of Holly Mack, IPR No. 2023-01251, Jun. 13, 2024.
Petitioner's Objections to Patent Owner's Response, IPR No. 2023-01251, May 30, 2024.
Notice of Stipulation, IPR No. 2023-01251, May 24, 2024.
Declaration of Aaron Striegel, Ph.D., in Support of Patent Owner's Response IPR No. 2023-01251, May 22, 2024.
Patent Owner's Response, IPR No. 2023-01251, May 22, 2024.
Deposition of Brian D. Gross, IPR No. 2023-01251, May 2, 2024.
Patent Owner's Updated Notice of Deposition of Brian D. Gross, IPR No. 2023-01251, Apr. 24, 2024.
Notice of Stipulation, IPR No. 2023-01251, Apr. 24, 2024.
Declaration of Andrew Ahmann M.D. in Support of Dexcom's Reply, IPR No. 2023-01251, Apr. 9, 2024.
Patent Owner's Notice of Deposition of Brian D. Gross, IPR No. 2023-01251, Apr. 2, 2024.
Notice of Final Written Decision re Inter Partes Review of the '649 Patent, IPR No. 2022-00605, Jul. 13, 2025.
Final Written Decision, IPR No. 2022-00605, Jul. 10, 2025.
Record of Oral Hearing, IPR No. 2022-00605, Apr. 26, 2023.
Joint Claim Construction Chart, Case No. 23-239-KAJ, Mar. 21, 2024.
Dexcom, Inc's Initial Proposed Claim Constructions, Case No. 23-239-KAJ, Feb. 28, 2024.
Complaint, Case No. 23-239-KAJ, Mar. 3, 2023.
Dexcom's Notice of Appeal, Case No. 21-CV-977-KAJ, Nov. 26, 2024.
Memorandum Opinion, Unsealed, Case No. 21-CV-977-KAJ, Nov. 21, 2024.
Order, Case No. 21-CV-977-KAJ, Nov. 21, 2024.
Order, Case No. 21-CV-977-KAJ, Nov. 13, 2024.
Memorandum Opinion, Sealed, Case No. 21-CV-977-KAJ, Nov. 13, 2024.
Exhibit 056-22 from DexCom, Inc.'s Final Invalidity Contentions, Case No. 21-CV-977-KAJ (D. Delaware), Sep. 19, 2024.
Exhibit 056-21 from DexCom, Inc.'s Final Invalidity Contentions, Case No. 21-CV-977-KAJ (D. Delaware), Sep. 19, 2024.
Exhibit 056-20 from DexCom, Inc.'s Final Invalidity Contentions, Case No. 21-CV-977-KAJ (D. Delaware), Sep. 19, 2024.
Exhibit 056-19 from DexCom, Inc.'s Final Invalidity Contentions, Case No. 21-CV-977-KAJ (D. Delaware), Sep. 19, 2024.
Exhibit 056-18 from DexCom, Inc.'s Final Invalidity Contentions, Case No. 21-CV-977-KAJ (D. Delaware), Sep. 19, 2024.
Exhibit 056-17 from DexCom, Inc.'s Final Invalidity Contentions, Case No. 21-CV-977-KAJ (D. Delaware), Sep. 19, 2024.
Exhibit 056-16 from DexCom, Inc.'s Final Invalidity Contentions, Case No. 21-CV-977-KAJ (D. Delaware), Sep. 19, 2024.
Exhibit 056-15 from DexCom, Inc.'s Final Invalidity Contentions, Case No. 21-CV-977-KAJ (D. Delaware), Sep. 19, 2024.
Exhibit 056-14 from DexCom, Inc.'s Final Invalidity Contentions, Case No. 21-CV-977-KAJ (D. Delaware), Sep. 19, 2024.
Exhibit 056-13 from DexCom, Inc.'s Final Invalidity Contentions, Case No. 21-CV-977-KAJ (D. Delaware), Sep. 19, 2024.
Exhibit 056-12 from DexCom, Inc.'s Final Invalidity Contentions, Case No. 21-CV-977-KAJ (D. Delaware), Sep. 19, 2024.
Exhibit 056-11 from DexCom, Inc.'s Final Invalidity Contentions, Case No. 21-CV-977-KAJ (D. Delaware), Sep. 19, 2024.
Exhibit 056-10 from DexCom, Inc.'s Final Invalidity Contentions, Case No. 21-CV-977-KAJ (D. Delaware), Sep. 19, 2024.
Exhibit 056-9 from DexCom, Inc.'s Final Invalidity Contentions, Case No. 21-CV-977-KAJ (D. Delaware), Sep. 19, 2024.

(56) References Cited

OTHER PUBLICATIONS

Exhibit 056-8 from DexCom, Inc.'s Final Invalidity Contentions, Case No. 21-CV-977-KAJ (D. Delaware), Sep. 19, 2024.
Exhibit 056-7 from DexCom, Inc.'s Final Invalidity Contentions, Case No. 21-CV-977-KAJ (D. Delaware), Sep. 19, 2024.
Exhibit 056-5 from DexCom, Inc.'s Final Invalidity Contentions, Case No. 21-CV-977-KAJ (D. Delaware), Sep. 19, 2024.
Exhibit 056-4 from DexCom, Inc.'s Final Invalidity Contentions, Case No. 21-CV-977-KAJ (D. Delaware), Sep. 19, 2024.
Exhibit 056-3 from DexCom, Inc.'s Final Invalidity Contentions, Case No. 21-CV-977-KAJ (D. Delaware), Sep. 19, 2024.
Reference PTX-0619 (Excerpted) of Dexcom's Reply in Support of Its Renewed Motion for Judgment as a Matter of Law and Motion for a New Trial, Case No. 21-CV-977-KAJ, Jul. 12, 2024.
Dexcom's Reply in Support of Its Renewed Motion for Judgment as a Matter of Law and Motion for a New Trial, Case No. 21-CV-977-KAJ, Jul. 12, 2024.
Plaintiffs' Reply Brief in Support of Their Motion for Judgment as a Matter of Law Under Federal Rule of Civil Procedure 50 and for a New Trial Under Federal Rule of Civil Procedure 59, Case No. 21-CV-977-KAJ (D. Delaware), Jul. 12, 2024.
Reference DX4961 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
Reference DX4756 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
Reference DX4721 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
Reference DX4720 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
Reference DX4719 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
Reference DX1550 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
Reference DX0179 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
Reference DX0012 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
Reference DDX-12 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
Reference DDX-8 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
Reference DDX-5 of Defendant Dexcom, Inc.'s Memorandum in Opposition to Plaintiffs' Motion for Judgment as a Matter of Law or, Alternatively, for a New Trial, Case No. 21-CV-977-KAJ (D. Delaware), Jun. 21, 2024.
Defendant Dexcom, Inc.'s Memorandum in Opposition to Plaintiffs' Motion for Judgment as a Matter of Law Or, Alternatively, for a New Trial, Case No. 21-CV-977-KAJ (D. Delaware), Jun. 21, 2024.
Reference DX4726 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
Reference DX4721 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
Reference DX4719 Defendant Dexcom, Inc.'s Appendix to Motion for Judgment as a Matter of Law or, Alternatively, for a New Trial, Case No. 21-CV-977-KAJ (D. Delaware), May 24, 2024.
Reference DX0381 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
Reference DX0189 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
Reference DX0183 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
Reference DX0012 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
Reference PDX07 of Defendant Dexcom, Inc.'s Appendix to Motion for Judgment as a Matter of Law or, Alternatively, for a New Trial, Case No. 21-CV-977-KAJ (D. Delaware)—Public Version, May 24, 2024.
Defendant Dexcom, Inc.'s Appendix to Motion for Judgment as a Matter of Law or, Alternatively, for a New Trial, Case No. 21-CV-977-KAJ (D. Delaware), May 24, 2024.
Plaintiffs' Opening Brief in Support of Their Motion for Judgment as a Matter of Law Under Federal Rule of Civil Procedure 50 and for a New Trial Under Federal Rule of Civil Procedure 59, Case No. 21-CV-977-KAJ (D. Delaware), May 24, 2024.
Defendant Dexcom, Inc.'s Opening Brief in Support of Its Renewed Motion for Judgment as a Matter of Law and Motion for New Trial, Case No. 21-CV-977-KAJ (D. Delaware), May 24, 2024.
Joint Status Report, Case No. 21-CV-977-KAJ (D. Delaware), May 7, 2024.
Plaintiffs' Renewed Motion for Judgment as a Matter of Law, Case No. 21-CV-977-KAJ (D. Delaware), Apr. 19, 2024.
Dexcom, Inc.'s Renewed Motion for Judgment as a Matter of Law and Motion for New Trial, Case No. 21-CV-977-KAJ (D. Delaware), Apr. 19, 2024.
Joint Status Report, Case No. 21-CV-977-KAJ (D. Delaware), Apr. 5, 2024.
Transcript of Jury Trial, vol. X, Case No. 21-CV-977-KAJ (D. Delaware), Mar. 22, 2024.
Transcript of Jury Trial, vol. IX, Case No. 21-CV-977-KAJ (D. Delaware), Mar. 21, 2024.
Transcript of Jury Trial, vol. VIII, Case No. 21-CV-977-KAJ (D. Delaware), Mar. 20, 2024.
Transcript of Jury Trial, Case No. 21-CV-977-KAJ (D. Delaware), Mar. 19, 2024.
Transcript of Jury Trial, vol. VI, Case No. 21-CV-977-KAJ (D. Delaware), Mar. 18, 2024.
Transcript of Jury Trial, vol. V, Case No. 21-CV-977-KAJ (D. Delaware), Mar. 15, 2024.
Transcript of Jury Trial, vol. IV, Case No. 21-CV-977-KAJ (D. Delaware), Mar. 14, 2024.
Transcript of Jury Trial, vol. III, Case No. 21-CV-977-KAJ (D. Delaware), Mar. 13, 2024.
Transcript of Jury Trial, vol. II, Case No. 21-CV-977-KAJ (D. Delaware), Mar. 12 2024.
Transcript of Jury Trial, vol. I, Case No. 21-CV-977-KAJ (D. Delaware), Mar. 11, 2024.
Declaration of Karl R. Leinsing, Msme, Pe, in Support of Abbott's Motion for Summary Judgement, Case No. 21-CV-977-KAJ (D. Delaware)—Public Version, May 19, 2023.

(56) References Cited

OTHER PUBLICATIONS

Memorandum Opinion and Order, Case No. 21-209-WCB, Mar. 3, 2023.
Declaration of Eugene E. Wright, Jr. MD, IPR No. 2024-00521., Dec. 6, 2024.
Declaration of Aaron Striegel, Ph.D, in Support of Patent Owner's Response, IPR No. 2024-00521., Dec. 6, 2024.
Deposition of Brian D. Gross, IPR No. 2024-00521.

METHODS AND SYSTEMS FOR EARLY SIGNAL ATTENUATION DETECTION AND PROCESSING

RELATED APPLICATIONS

The present application is a continuation of U.S. patent application Ser. No. 17/411,154, filed Aug. 25, 2021, which is a continuation of U.S. patent application Ser. No. 17/245,719, filed Apr. 30, 2021, now U.S. patent Ser. No. 11/116,431, which is a continuation of U.S. patent application Ser. No. 16/228,910, filed Dec. 21, 2018, now U.S. Pat. No. 11,013,431, which is a continuation of U.S. patent application Ser. No. 15/061,774, filed Mar. 4, 2016, now U.S. Pat. No. 10,194,844, which is a continuation of U.S. patent application Ser. No. 13/925,694, filed Jun. 24, 2013, now U.S. Pat. No. 9,310,230, which is a continuation of U.S. patent application Ser. No. 12/769,635, filed Apr. 28, 2010, now U.S. Pat. No. 8,483,967, which claims the benefit of U.S. Provisional Patent Application No. 61/173,600, filed Apr. 29, 2009, the disclosures of all of which are incorporated herein by reference in their entireties for all purposes.

BACKGROUND

Analyte, e.g., glucose monitoring systems including continuous and discrete monitoring systems generally include a small, lightweight battery powered and microprocessor controlled system which is configured to detect signals proportional to the corresponding measured glucose levels using an electrometer. RF signals may be used to transmit the collected data. One aspect of certain analyte monitoring systems includes a transcutaneous or subcutaneous analyte sensor configuration which is, for example, at least partially positioned through the skin layer of a subject whose analyte level is to be monitored. The sensor may use a two or three-electrode (work, reference and counter electrodes) configuration driven by a controlled potential (potentiostat) analog circuit connected through a contact system.

An analyte sensor may be configured so that a portion thereof is placed under the skin of the patient so as to contact analyte of the patient, and another portion or segment of the analyte sensor may be in communication with the transmitter unit. The transmitter unit may be configured to transmit the analyte levels detected by the sensor over a wireless communication link such as an RF (radio frequency) communication link to a receiver/monitor unit. The receiver/monitor unit may perform data analysis, among other functions, on the received analyte levels to generate information pertaining to the monitored analyte levels.

SUMMARY

Devices and methods for analyte monitoring, e.g., glucose monitoring, and/or therapy management system including, for example, medication infusion devices are provided. Embodiments include transmitting information from a first location to a second, e.g., using a telemetry system such as RF telemetry. Systems herein include continuous analyte monitoring systems, discrete analyte monitoring system, and therapy management systems.

Embodiments include receiving sensor data from an analyte sensor of a sensor monitoring system, processing the received sensor data with time corresponding calibration data, outputting the processed sensor data, detecting one or more adverse conditions associated with the sensor monitoring system, disabling the output of the sensor data during a adverse condition time period, determining that the one or more detected adverse conditions is no longer present in the sensor monitoring system, retrieving the sensor data during the adverse condition time period, processing the retrieved sensor data during the adverse condition time period, and outputting the processed retrieved sensor data.

Embodiments include detecting a condition unsuitable for calibration of an analyte sensor for a predetermined time period, disabling output of information associated with the analyte sensor, determining a successful calibration of the analyte sensor, retrieving one or more parameters associated with the successful calibration, processing sensor data during the time period of disabled output of information with the one or more parameters associated with the successful calibration, and displaying the processed sensor data for the time period of disabled information output.

Embodiments include an interface configured to receive sensor data, a first memory configured to store the received sensor data, a processor coupled to the memory and configured to process the stored sensor data, a second memory coupled to the processor and configured to store the processed sensor data, and a display unit coupled to the second memory and configured to display the processed sensor data, where the processor is further configured to detect a condition unsuitable for calibration of a sensor for a predetermined time period, disable display of processed sensor data, determine a successful calibration of the sensor, retrieve one or more parameters associated with the successful calibration, process the sensor data during the time period of disabled display of sensor data with the one or more parameters associated with the successful calibration, and display the processed sensor data for the time period of disabled information output.

These and other objects, features and advantages of the present disclosure will become more fully apparent from the following detailed description of the embodiments, the appended claims and the accompanying drawings.

INCORPORATION BY REFERENCE

The following patents, applications and/or publications are incorporated herein by reference for all purposes: U.S. Pat. Nos. 4,545,382; 4,711,245; 5,262,035; 5,262,305; 5,264,104; 5,320,715; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,167,818; and 7,299,082; U.S. Published Application Nos. 2004/0186365; 2005/0182306; 2007/0056858; 2007/0068807; 2007/0227911; 2007/0233013; 2008/0081977; 2008/0161666; and 2009/0054748; U.S. patent application Ser. Nos. 11/831,866; 11/831,881; 11/831,895; 12/102,839; 12/102,844; 12/102,847; 12/102,855; 12/102,856; 12/152,636; 12/152,648; 12/152,650; 12/152,652; 12/152,657; 12/152,662; 12/152,670; 12/152,673; 12/363,712; 12/131,012; 12/242,823; 12/363,712; 12/393,921; 12/495,709; 12/698,124; 12/699,653; 12/699,844; 12/714,439; 12/761,372; and 12/761,387 and U.S. Provisional Application Nos. 61/230,686 and 61/227,967.

DETAILED DESCRIPTION

Figure 1:
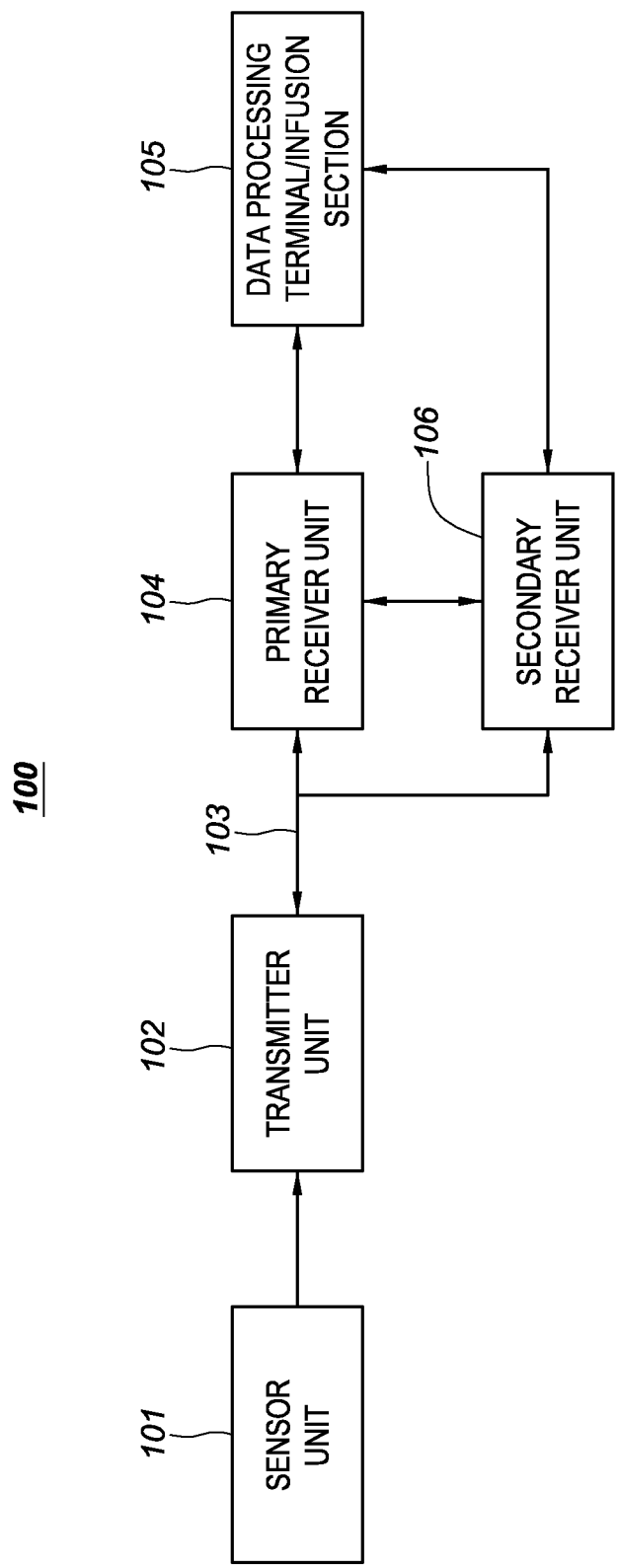
FIG. 1 illustrates a block diagram of a data monitoring and management system for practicing one or more embodiments of the present disclosure.

Before the present disclosure is described in additional detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

As described in further detail below, in accordance with the various embodiments of the present disclosure, there is provided a method and system for positioning a controller unit within a transmission range for close proximity communication, transmitting one or more predefined close proximity commands, and receiving a response packet in response to the transmitted one or more predefined close proximity commands. For example, in one aspect, close proximity communication includes short range wireless communication between communication components or devices, where the communication range is limited to about 10 inches or less, about 5 inches or less, or about 2 inches or less, or other suitable, short range or distance between the devices. The close proximity wireless communication in certain embodiments includes a bi-directional communication where a command sending communication device, when positioned within the short communication range or in close proximity to the command receiving communication device, is configured to transmit one or more commands to the command receiving communication device (for example, when a user activates or actuates a transmit command button or switch). In response, the command receiving communication device may be configured to perform one or more routines associated with the received command, and/or return or send back a response data packet or signal to the command sending communication device. Example of such functions and or commands may include, but not limited to activation of certain functions or routines such as analyte related data processing, and the like.

FIG. 1 illustrates a data monitoring and management system such as, for example, analyte (e.g., glucose) monitoring system 100 in accordance with one embodiment of the present disclosure. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. More than one analyte may be monitored by a single system, e.g., a single analyte sensor.

The analyte monitoring system 100 includes a sensor unit 101, a data processing and transmitter unit 102 coupleable to the sensor unit 101, and a primary receiver unit 104 which is configured to communicate with the data processing and transmitter unit 102 via a bi-directional communication link 103. The primary receiver unit 104 may be further configured to transmit data to a data processing terminal 105 for evaluating the data received by the primary receiver unit 104. Moreover, the data processing terminal 105 in one embodiment may be configured to receive data directly from the data processing and transmitter unit 102 via a communication link which may optionally be configured for bi-directional communication. Accordingly, data processing and transmitter unit 102 and/or receiver unit 104 may include a transceiver.

Also shown in FIG. 1 is an optional secondary receiver unit 106 which is operatively coupled to the communication link and configured to receive data transmitted from the data processing and transmitter unit 102. Moreover, as shown in the Figure, the secondary receiver unit 106 is configured to communicate with the primary receiver unit 104 as well as the data processing terminal 105. Indeed, the secondary receiver unit 106 may be configured for bi-directional wireless communication with each or one of the primary receiver unit 104 and the data processing terminal 105. As discussed in further detail below, in one embodiment of the present disclosure, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, pager, mobile phone, PDA, for example. Alternatively, the secondary receiver unit 106 may be configured with the same or substantially similar functionality as the primary receiver unit 104. The receiver unit may be configured to be used in conjunction with a docking cradle unit, for example for one or more of the following or other functions: placement by bedside, for re-charging, for data management, for night time monitoring, and/or bi-directional communication device.

In one aspect sensor unit 101 may include two or more sensors, each configured to communicate with data processing and transmitter unit 102. Furthermore, while only one, data processing and transmitter unit 102, communication link 103, and data processing terminal 105 are shown in the embodiment of the analyte monitoring system 100 illustrated in FIG. 1. However, it will be appreciated by one of ordinary skill in the art that the analyte monitoring system 100 may include one or more sensors, multiple transmitter units 102, communication links 103, and data processing terminals 105. Moreover, within the scope of the present disclosure, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present disclosure, the sensor unit 101 is physically positioned in or on the body of a user whose analyte level is being monitored. The sensor unit 101 may be configured to continuously sample the analyte level of the user and convert the sampled analyte level into a corresponding data signal for transmission by the data processing and transmitter unit 102. In certain embodiments, the data processing and transmitter unit 102 may be physically coupled to the sensor unit 101 so that both devices are integrated in a single housing and positioned on the user's body. The data processing and transmitter unit 102 may perform data processing such as filtering and encoding on data signals and/or other functions, each of which corresponds to a sampled analyte level of the user, and in any event data processing and transmitter unit 102 transmits analyte information to the primary receiver unit 104 via the communication link 103. Examples of such integrated sensor and transmitter units can be found in, among others, U.S. patent application Ser. No. 12/698,124, incorporated herein by reference.

In one embodiment, the analyte monitoring system 100 is configured as a one-way RF communication path from the data processing and transmitter unit 102 to the primary receiver unit 104. In such embodiment, the data processing and transmitter unit 102 transmits the sampled data signals received from the sensor unit 101 without acknowledgement from the primary receiver unit 104 that the transmitted sampled data signals have been received. For example, the data processing and transmitter unit 102 may be configured to transmit the encoded sampled data signals at a fixed rate (e.g., at one minute intervals) after the completion of the initial power on procedure. Likewise, the primary receiver unit 104 may be configured to detect such transmitted encoded sampled data signals at predetermined time intervals. Alternatively, the analyte monitoring system 100 may be configured with a bi-directional RF (or otherwise) communication between the data processing and transmitter unit 102 and the primary receiver unit 104.

Additionally, in one aspect, the primary receiver unit 104 may include two sections. The first section is an analog interface section that is configured to communicate with the data processing and transmitter unit 102 via the communication link 103. In one embodiment, the analog interface section may include an RF receiver and an antenna for receiving and amplifying the data signals from the data processing and transmitter unit 102, which are thereafter, demodulated with a local oscillator and filtered through a band-pass filter. The second section of the primary receiver unit 104 is a data processing section which is configured to process the data signals received from the data processing and transmitter unit 102 such as by performing data decoding, error detection and correction, data clock generation, and data bit recovery.

In operation, upon completing the power-on procedure, the primary receiver unit 104 is configured to detect the presence of the data processing and transmitter unit 102 within its range based on, for example, the strength of the detected data signals received from the data processing and transmitter unit 102 and/or a predetermined transmitter identification information. Upon successful synchronization with the corresponding data processing and transmitter unit 102, the primary receiver unit 104 is configured to begin receiving from the data processing and transmitter unit 102 data signals corresponding to the user's detected analyte level. More specifically, the primary receiver unit 104 in one embodiment is configured to perform synchronized time hopping with the corresponding synchronized data processing and transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present disclosure, the data processing terminal 105 may include an infusion device such as an insulin infusion pump (external or implantable) or the like, which may be configured to administer insulin to patients, and which may be configured to communicate with the receiver unit 104 for receiving, among others, the measured analyte level. Alternatively, the receiver unit 104 may be configured to integrate or otherwise couple to an infusion device therein so that the receiver unit 104 is configured to administer insulin therapy to patients, for example, for administering and modifying basal profiles, as well as for determining appropriate boluses for administration based on, among others, the detected analyte levels received from the data processing and transmitter unit 102.

Additionally, the data processing and transmitter unit 102, the primary receiver unit 104 and the data processing terminal 105 may each be configured for bi-directional wireless communication such that each of the data processing and transmitter unit 102, the primary receiver unit 104 and the data processing terminal 105 may be configured to communicate (that is, transmit data to and receive data from) with each other via the wireless communication link 103. More specifically, the data processing terminal 105 may in one embodiment be configured to receive data directly from the data processing and transmitter unit 102 via the communication link 103, where the communication link 103, as described above, may be configured for bi-directional communication.

In this embodiment, the data processing terminal 105 which may include an insulin pump, may be configured to receive the analyte signals from the data processing and transmitter unit 102, and thus, incorporate the functions of the receiver 104 including data processing for managing the patient's insulin therapy and analyte monitoring. In one embodiment, the communication link 103 may include one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPPA requirements) while avoiding potential data collision and interference.

Figure 2:
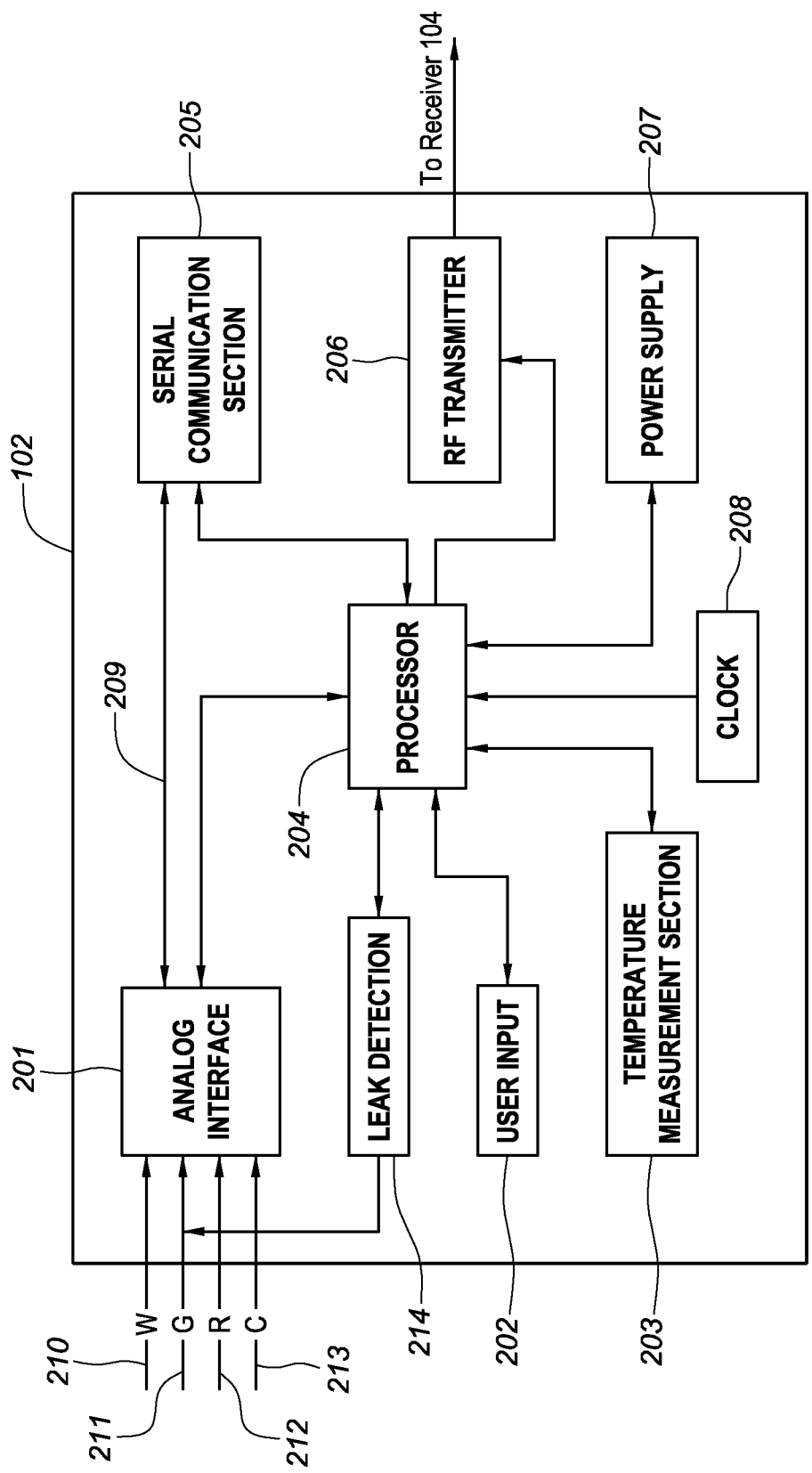
FIG. 2 is a block diagram of the transmitter unit of the data monitoring and management system shown in FIG. 1 in accordance with one embodiment of the present disclosure.

FIG. 2 is a block diagram of the transmitter of the data monitoring and detection system shown in FIG. 1 in accordance with one embodiment of the present disclosure. Referring to the Figure, the data processing and transmitter unit 102 in one embodiment includes an analog interface 201 configured to communicate with the sensor unit 101 (FIG. 1), a user input 202, and a temperature measurement section 203, each of which is operatively coupled to a transmitter processor 204 such as a central processing unit (CPU). As can be seen from FIG. 2, there are provided four contacts, three of which are electrodes—work electrode (W) 210, guard contact (G) 211, reference electrode (R) 212, and counter electrode (C) 213, each operatively coupled to the analog interface 201 of the data processing and transmitter unit 102 for connection to the sensor unit 101 (FIG. 1). In one embodiment, each of the work electrode (W) 210, guard contact (G) 211, reference electrode (R) 212, and counter electrode (C) 213 may be made using a conductive material that is either printed or etched or ablated, for example, such as carbon which may be printed, or a metal such as a metal foil (e.g., gold) or the like, which may be etched or ablated or otherwise processed to provide one or more electrodes. Fewer or greater electrodes and/or contact may be provided in certain embodiments.

Further shown in FIG. 2 are a transmitter serial communication section 205 and an RF transmitter 206, each of which is also operatively coupled to the transmitter processor 204. Moreover, a power supply 207 such as a battery is also provided in the data processing and transmitter unit 102 to provide the necessary power for the data processing and transmitter unit 102. In certain embodiments, the power supply 207 also provides the power necessary to power the sensor 101. In other embodiments, the sensor is a self-powered sensor, such as the sensor described in U.S. patent application Ser. No. 12/393,921, incorporated herein by reference. Additionally, as can be seen from the Figure, clock 208 is provided to, among others, supply real time information to the transmitter processor 204.

In one embodiment, a unidirectional input path is established from the sensor unit 101 (FIG. 1) and/or manufacturing and testing equipment to the analog interface 201 of the data processing and transmitter unit 102, while a unidirectional output is established from the output of the RF transmitter 206 of the data processing and transmitter unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the data processing and transmitter unit 102 is configured to transmit to the primary receiver unit 104 (FIG. 1), via the communication link 103 (FIG. 1), processed and encoded data signals received from the sensor unit 101 (FIG. 1). Additionally, the unidirectional communication data path between the analog interface 201 and the RF transmitter 206 discussed above allows for the configuration of the data processing and transmitter unit 102 for operation upon completion of the manufacturing process as well as for direct communication for diagnostic and testing purposes.

As discussed above, the transmitter processor 204 is configured to transmit control signals to the various sections of the data processing and transmitter unit 102 during the operation of the data processing and transmitter unit 102. In one embodiment, the transmitter processor 204 also includes a memory (not shown) for storing data such as the identification information for the data processing and transmitter unit 102, as well as the data signals received from the sensor unit 101. The stored information may be retrieved and processed for transmission to the primary receiver unit 104 under the control of the transmitter processor 204. Furthermore, the power supply 207 may include a commercially available battery, which may be a rechargeable battery.

In certain embodiments, the data processing and transmitter unit 102 is also configured such that the power supply section 207 is capable of providing power to the transmitter for a minimum of about three months of continuous operation, e.g., after having been stored for about eighteen months such as stored in a low-power (non-operating) mode. In one embodiment, this may be achieved by the transmitter processor 204 operating in low power modes in the non-operating state, for example, drawing no more than approximately 1 µA of current. Indeed, in one embodiment, a step during the manufacturing process of the data processing and transmitter unit 102 may place the data processing and transmitter unit 102 in the lower power, non-operating state (i.e., post-manufacture sleep mode). In this manner, the shelf life of the data processing and transmitter unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present disclosure, the power supply unit 207 is configured to provide the necessary power to each of the components of the data processing and transmitter unit 102 shown in FIG. 2.

Referring back to FIG. 2, the power supply section 207 of the data processing and transmitter unit 102 in one embodiment may include a rechargeable battery unit that may be recharged by a separate power supply recharging unit (for example, provided in the receiver unit 104) so that the data processing and transmitter unit 102 may be powered for a longer period of usage time. Moreover, in one embodiment, the data processing and transmitter unit 102 may be configured without a battery in the power supply section 207, in which case the data processing and transmitter unit 102 may be configured to receive power from an external power supply source (for example, a battery) as discussed in further detail below.

Referring yet again to FIG. 2, the temperature measurement section 203 of the data processing and transmitter unit 102 is configured to monitor the temperature of the skin near the sensor insertion site. The temperature reading is used to adjust the analyte readings obtained from the analog interface 201. In certain embodiments, the RF transmitter 206 of the transmitter unit 102 may be configured for operation in the frequency band of approximately 315 MHz to approximately 322 MHz, for example, in the United States. In certain embodiments, the RF transmitter 206 of the transmitter unit 102 may be configured for operation in the frequency band of approximately 400 MHz to approximately 470 MHz. Further, in one embodiment, the RF transmitter 206 is configured to modulate the carrier frequency by performing Frequency Shift Keying and Manchester encoding. In one embodiment, the data transmission rate is about 19,200 symbols per second, with a minimum transmission range for communication with the primary receiver unit 104.

Referring yet again to FIG. 2, also shown is a leak detection circuit 214 coupled to the guard electrode (G) 211 and the processor 204 in the transmitter unit 102 of the data monitoring and management system 100. The leak detection circuit 214 in accordance with one embodiment of the present disclosure may be configured to detect leakage current in the sensor unit 101 to determine whether the measured sensor data are corrupt or whether the measured data from the sensor 101 is accurate. Exemplary analyte systems that may be employed are described in, for example, U.S. Pat. Nos. 6,134,461, 6,175,752, 6,121,611, 6,560,471, 6,746,582, and elsewhere, the disclosure of each of which are incorporated by reference for all purposes.

Figure 3:
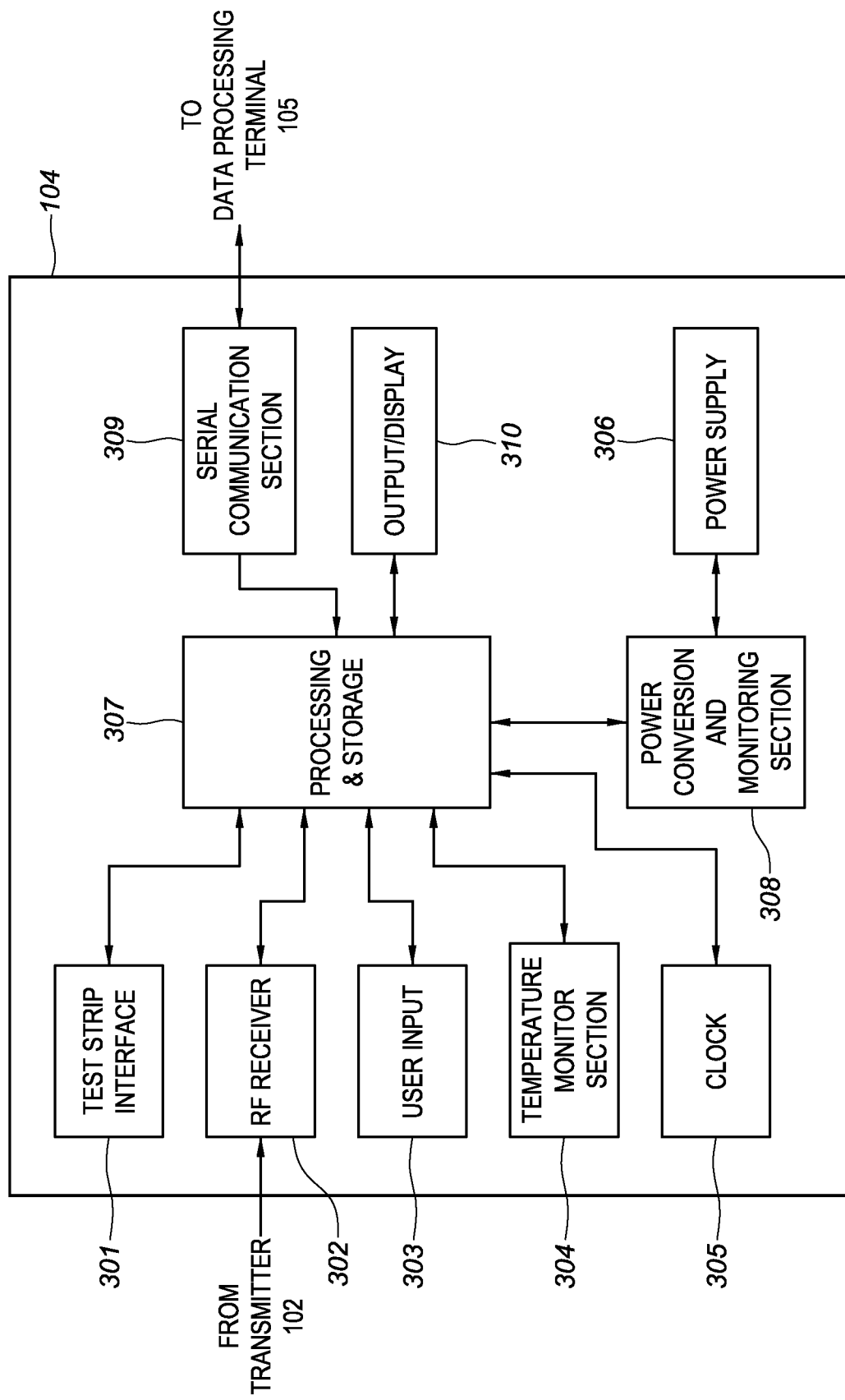
FIG. 3 is a block diagram of the receiver/monitor unit of the data monitoring and management system shown in FIG. 1 in accordance with one embodiment of the present disclosure.

FIG. 3 is a block diagram of the receiver/monitor unit of the data monitoring and management system shown in FIG. 1 in accordance with one embodiment of the present disclosure. Referring to FIG. 3, the primary receiver unit 104 includes an analyte test strip, e.g., blood glucose test strip, interface 301, an RF receiver 302, an input 303, a temperature monitor section 304, and a clock 305, each of which is operatively coupled to a receiver processor 307. As can be further seen from the Figure, the primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the receiver processor 307.

In one embodiment, the test strip interface 301 includes a glucose level testing portion to receive a manual insertion of a glucose test strip, and thereby determine and display the glucose level of the test strip on the output 310 of the primary receiver unit 104. This manual testing of glucose may be used to calibrate the sensor unit 101 or otherwise.

The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the primary receiver unit 104 is configured to allow the user to enter information into the primary receiver unit 104 as needed. In one aspect, the input 303 may include one or more keys of a keypad, a touch-sensitive screen, or a voice-activated input command unit. The temperature monitor section 304 is configured to provide temperature information of the primary receiver unit 104 to the receiver processor 307, while the clock 305 provides, among others, real time information to the receiver processor 307.

Each of the various components of the primary receiver unit 104 shown in FIG. 3 is powered by the power supply 306 which, in one embodiment, includes a battery. Furthermore, the power conversion and monitoring section 308 is configured to monitor the power usage by the various components in the primary receiver unit 104 for effective power management and to alert the user, for example, in the event of power usage which renders the primary receiver unit 104 in sub-optimal operating conditions. An example of such sub-optimal operating condition may include, for example, operating the vibration output mode (as discussed below) for a period of time thus substantially draining the power supply 306 while the processor 307 (thus, the primary receiver unit 104) is turned on. Moreover, the power conversion and monitoring section 308 may additionally be configured to include a reverse polarity protection circuit such as a field effect transistor (FET) configured as a battery activated switch.

The serial communication section 309 in the primary receiver unit 104 is configured to provide a bi-directional communication path from the testing and/or manufacturing equipment for, among others, initialization, testing, and configuration of the primary receiver unit 104. Serial communication section 104 can also be used to upload data to a computer, such as time-stamped blood glucose data. The communication link with an external device (not shown) can be made, for example, by cable, infrared (IR) or RF link. The output 310 of the primary receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the primary receiver unit 104 also includes an electro-luminescent lamp configured to provide backlighting to the output 310 for output visual display in dark ambient surroundings.

Referring back to FIG. 3, the primary receiver unit 104 in one embodiment may also include a storage section such as a programmable, non-volatile memory device as part of the processor 307, or provided separately in the primary receiver unit 104, operatively coupled to the processor 307. The processor 307 may be configured to synchronize with a transmitter, e.g., using Manchester decoding or the like, as well as error detection and correction upon the encoded data signals received from the transmitter unit 102 via the communication link 103.

Periodic calibration of the sensor unit 101 (FIG. 1) of an analyte monitoring system 100, in some embodiments, may be required for accurate calculation of a user's analyte level. Calibration, in some aspects, is used to ensure the analyte related data signals received at a transmitter unit 102 (and further transmitted to a receiver unit, such as the primary receiver unit 104) are correctly converted to corresponding analyte levels. Exemplary calibration protocols, routines and techniques are described, for example, in U.S. Pat. No. 7,299,082, U.S. patent application Ser. No. 11/537,991 filed Oct. 2, 2006, U.S. patent application Ser. No. 12/363,706 filed Jan. 30, 2009, and in U.S. patent application Ser. No. 12/363,712 filed Jan. 30, 2009, the disclosures of each of which are herein incorporated by reference for all purposes.

There are time periods where the sensor characteristics or the user's physiological condition renders the condition unsuitable for a sensor calibration event. For example, the sensor may be configured for periodic calibration, such as, after 2 hours after insertion, 10 hours after insertion, 12 hours after insertion, 24 hours after insertion, 48 hours after insertion, or 72 hours after insertion, or one or more combinations thereof. If a predetermined calibration event is triggered but a successful calibration does not result, after a certain time period (for example, a predetermined grace period during which to calibrate), the receiver unit may no longer display the monitored and processed glucose information.

Other conditions may also result in rendering the condition unsuitable for sensor calibration including, but not limited to, detection of a failure mode of a sensor, sensor data values being outside a predetermined range, rate of change of sensor data values being above a predetermined threshold, a temperature measurement outside a predetermined range, or any combination thereof.

Figure 4:
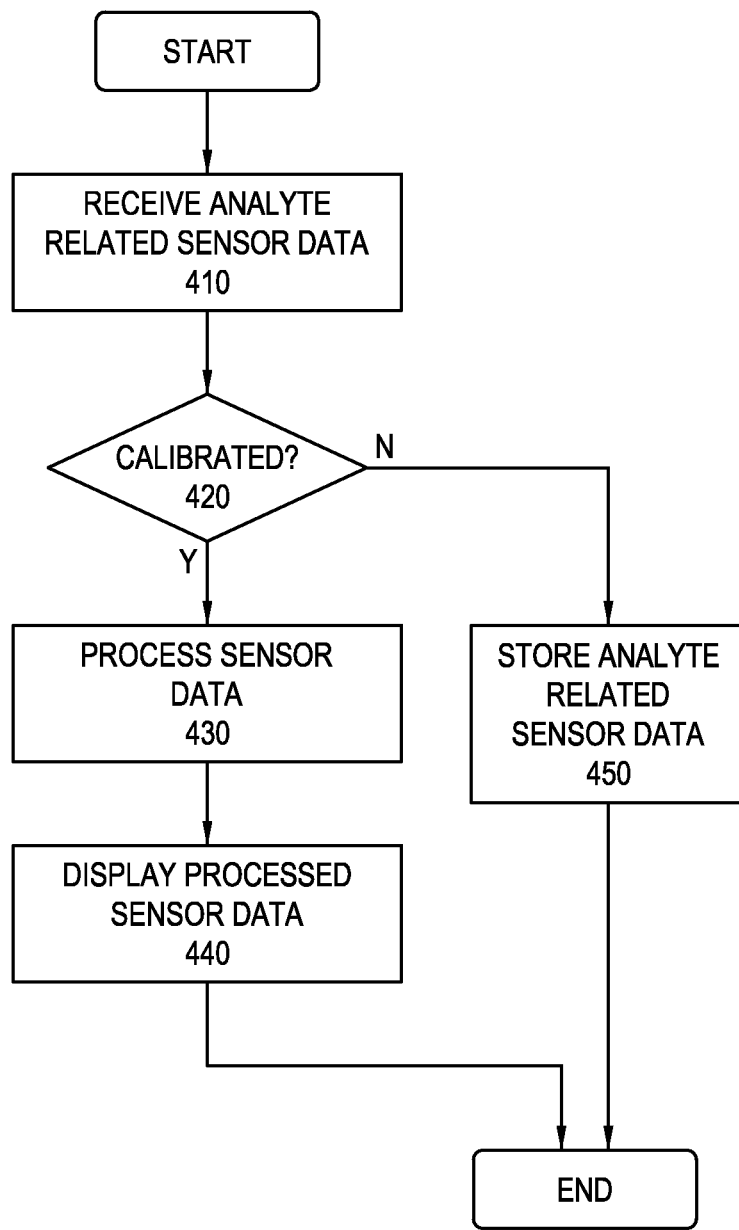
FIG. 4 illustrates analyte sensor data processing in accordance with one embodiment of the present disclosure.

FIG. 4 illustrates analyte sensor data processing in accordance with one embodiment of the present disclosure. Referring to FIG. 4, a transmitter unit 102 (FIG. 1) in operational contact with a sensor 101 receives analyte related sensor data (410) corresponding to a measured level of a biological fluid of the user. For example, the sensor 101 (FIG. 1) may be an analyte sensor configured to detect and measure the concentration of an analyte in a biological fluid, such as the blood of a user. Upon receipt of the analyte related sensor data, the transmitter unit 102 further transmits the analyte related sensor data to a receiver unit, such as primary receiver unit 104 (FIG. 1). It is to be noted that the reference to analyte related sensor data herein and throughout specification includes, for example, current signal received from the analyte sensor, as well as the current signal which has undergone predetermined data processing routines including, for example, filtering, clipping, digitizing, and/or encoding, and/or any other further processing and/or conditioning. In one aspect, the primary receiver unit 104 determines whether the sensor is calibrated and is in acceptable condition for further data processing (420). When sensor related conditions are unsuitable for calibration, the analyte related sensor data is stored (450) in a memory, for example, in the primary receiver unit 104.

Referring still to FIG. 4, if the sensor data is calibrated and in condition for further data processing, the sensor data is further processed (430) and output for display (440) to a user on a display unit 310 (FIG. 3) of the primary receiver unit 104. In one embodiment, the display of the processed sensor data comprises a graphical representation of the processed sensor data. In other embodiments, the processed sensor data may be displayed as numerical values, visual indicators, auditory outputs, or combinations thereof. In one aspect, the processing routine described in conjunction with FIG. 4 is performed or executed in, for example, the transmitter unit 102, the secondary receiver unit 106 (FIG. 1), or the data processing terminal 105 (FIG. 1) of the analyte monitoring system 100 (FIG. 1) based on analyte data received from the sensor 101.

Figure 5:
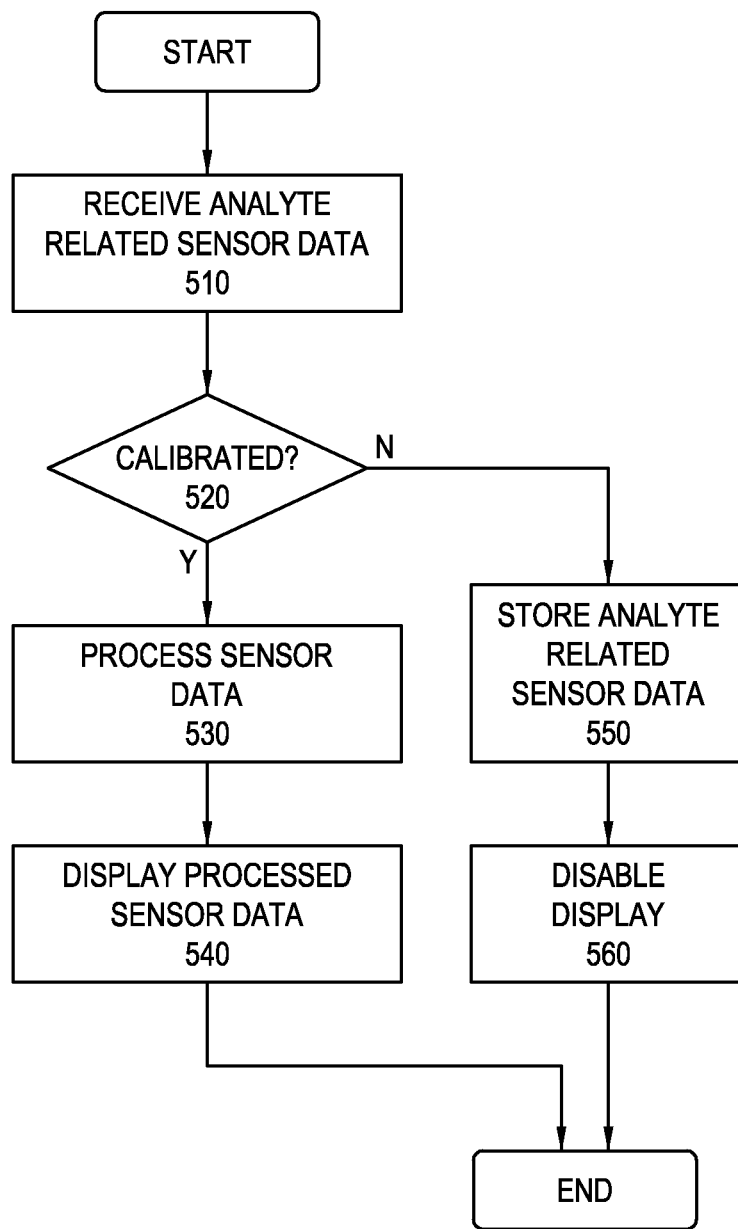
FIG. 5 illustrates analyte sensor data processing in accordance with one embodiment of the present disclosure.

FIG. 5 illustrates analyte sensor data processing in accordance with one embodiment of the present disclosure. Referring to FIG. 5, in one embodiment, transmitter unit 102 (FIG. 1) receives analyte related sensor data (510) from a sensor 101 (FIG. 1). Upon receipt of the analyte related sensor data, the transmitter unit 102 transmits the analyte related sensor data (or processed, digitized, and/or filtered signals) to the primary receiver unit 104 (FIG. 1). The primary receiver unit 104 is configured to determine if calibration of the sensor data is suitable—that is, whether the conditions necessary for sensor calibration are met (520).

Still referring to FIG. 5, if it is determined that the sensor 101 is not calibrated or calibration condition for calibrating the sensor 101 is not met, in one aspect, the primary receiver unit stores the analyte related sensor data in a memory (550) and temporarily disables display of the sensor data (560) to the user (for example, if a calibration event has not occurred and the calibration grace period has expired). On the other hand, if the sensor 101 is calibrated, the sensor data is processed (530) by the primary receiver unit 104 and the processed sensor data is output to the user (540), for example via a display unit 310 (FIG. 3) of the primary receiver unit 104. In one aspect, the processing routine described in conjunction with FIG. 5 is performed or executed in, for example, the transmitter unit 102, the secondary receiver unit 106, or the data processing terminal 105 of the analyte monitoring system 100 based on analyte data received from the sensor 101 (FIG. 1).

Figure 7A:
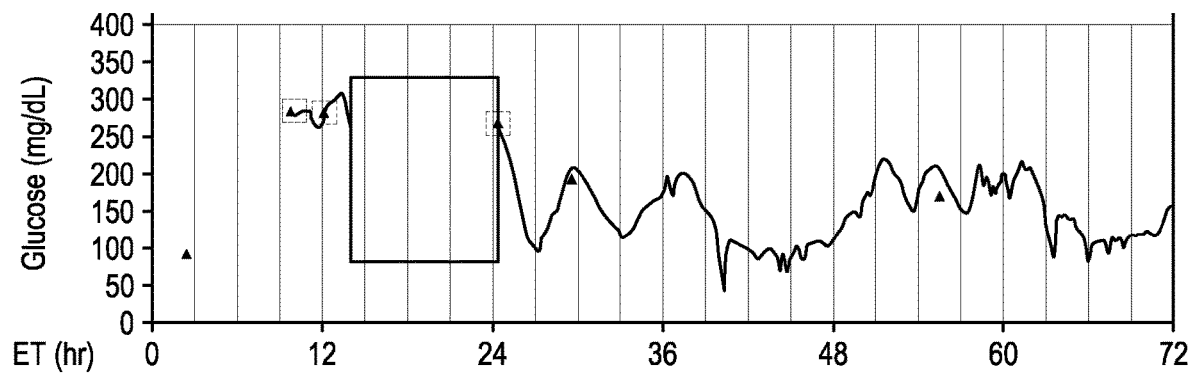
FIGS. 7A and 7B illustrate backfill of gaps of a period of uncalibrated sensor data in one embodiment.

In one aspect, the display or output of processed sensor data may be disabled if a required calibration event is unsuccessful over a permitted time period (for example, including a predetermined grace period measured from the scheduled calibration). Thereafter, upon successful calibration, the system resumes display of the processed and calibrated analyte sensor data. However, there may be a time period or a gap in the output display during which the necessary calibration did not occur in a timely manner. For example, as shown in FIG. 7A, if sensor data is displayed as a graphical display, during time periods where the analyte monitoring system 100 was not properly calibrated, analyte related sensor data was not processed and/or displayed, resulting in a gap in the graphical display.

Figure 6:
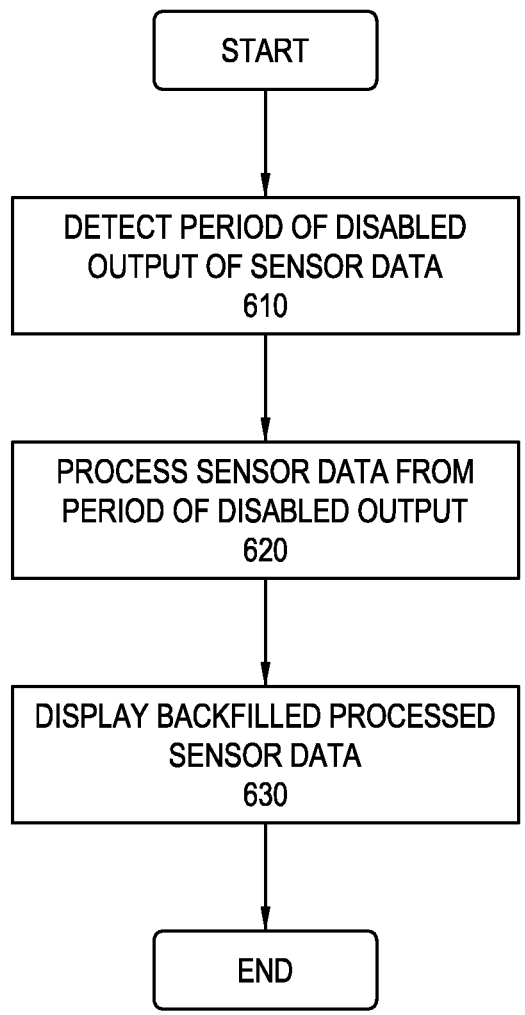
FIG. 6 illustrates backfilling gaps in sensor data in one embodiment of the present disclosure.

FIG. 6 illustrates backfilling gaps in sensor data in one embodiment of the present disclosure. Referring to FIG. 6, when a scheduled calibration event fails and the associated grace period for calibration does not occur, the output display of the processed, calibrated sensor data is disabled (610). Referring to FIG. 6, once the system recovers after a successful calibration event, the calibrated sensor data is once again displayed (and stored). Furthermore, in one aspect, based on the parameters associated with the successful calibration, the previously unprocessed data during the display time out period may be retrieved (for example, the previously stored analyte related sensor signals during this period) and processed using calibration data, such as a sensitivity ratio for conversion of analyte related sensor data to analyte levels. For example, in one aspect, the subset of analyte related sensor data that were previously unprocessed or uncalibrated due to unsuccessful contemporaneous calibration may be processed using, for example, calibration data such as the sensitivity ratio determined from the most recent successful calibration event, and thereafter, the gap in output display illustrating the processed and calibrated signals may be filled.

Figure 7B:
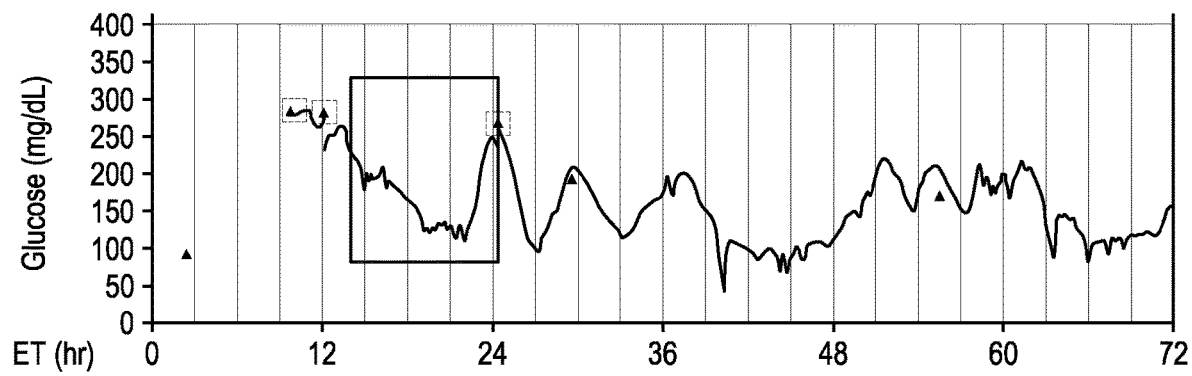

In one aspect, once successful calibration of the sensor data occurs, the calibration parameters from this calibration event may be used to process the sensor data during the period of disabled output or display (620). Upon successful processing of the sensor data during the period of disabled output, the processed sensor data during this time period is backfilled, or the gap in the processed continuous sensor data are filled in the display (630). By way of an example, FIGS. 7A and 7B illustrate the replacement of a period of unprocessed sensor data with corresponding backfilled processed sensor data, in one embodiment.

In one embodiment, the backfilled processed sensor data is displayed immediately upon calculation. In another embodiment, the backfilled processed sensor data is not displayed immediately, but rather, after waiting a predetermined period of time. The backfilled processed sensor data may not be displayed immediately to avoid possible unnecessary or incorrect action by a user in response to the backfilled processed sensor data. In this manner, in one aspect, the user or a healthcare provider may be provided with a continuous set of analyte data from the analyte monitoring system without any gaps in the processed signals for further analysis and/or therapy management.

In this manner, in accordance with the embodiments of the present disclosure, gaps in monitored analyte levels using an analyte monitoring system due to, for example, inability to promptly calibrate the sensor, system malfunction, sensor dislodging, signal errors associated with the sensor, transmitter unit, receiver unit, and the like, or any other variables or parameters that result in the inability of the analyte monitoring system to display or output the real-time monitored analyte level, may be retrospectively filled or reprocessed so that the data gap is closed and the continuously monitored analyte level does not have any or substantially missing data. That is, in embodiments of the present disclosure, upon correction or rectification of the condition or conditions/parameters which resulted in the analyte monitoring system disabling the output results associated with the monitored real time analyte levels, the parameters associated with the correction or rectification may be used to retrospectively correct or process data or signals so that the missing gaps in analyte related data may be processed and backfilled.

In this manner, advantageously, in aspects of the present disclosure, additional robustness may be provided to the user and/or the healthcare provider to improve therapy or health management decisions.

In one embodiment, a method may include receiving sensor data from an analyte sensor of a sensor monitoring system, processing the received sensor data with time corresponding calibration data, outputting the processed sensor data, detecting one or more adverse conditions associated with the sensor monitoring system, disabling the output of the sensor data during an adverse condition time period, determining that the one or more detected adverse conditions is no longer present in the sensor monitoring system, retrieving the sensor data during the adverse condition time period, processing the retrieved sensor data during the adverse condition time period, and outputting the processed retrieved sensor data.

In one aspect, outputting the processed sensor data may include displaying the sensor data in one or more of a graphical, numerical, pictorial, audible, vibratory, or one or more combinations thereof.

The one or more detected adverse conditions may include one or more of a sensor instability condition, a calibration failure condition, or a monitoring system failure condition.

The sensor instability condition may include one or more of an early signal attenuation condition of the sensor, sensor misposition error, sensor communication error, temperature measurement outside a predetermined range, or a combination thereof.

The calibration failure condition may include one or more of an analyte level exceeding a predetermined threshold, a rate of change of analyte level exceeding a predetermined threshold, a signal error associated with the reference data, a data unavailability condition, or a combination thereof.

Furthermore, the method may include storing the processed sensor data with the associated time information based on the analyte level detection time by the sensor.

In another embodiment, a method may include detecting a condition unsuitable for calibration of an analyte sensor for a predetermined time period, disabling output of information associated with the analyte sensor, determining a successful calibration of the analyte sensor, retrieving one or more parameters associated with the successful calibration, processing sensor data during the time period of disabled output of information with the one or more parameters associated with the successful calibration, and displaying the processed sensor data for the time period of disabled information output.

The sensor data may be analyte concentration data.

The analyte concentration data may include blood glucose concentration data.

The sensor data may be processed in substantially real-time.

The condition unsuitable for calibration may include one or more of a failure mode of a sensor, sensor data outside a predetermined acceptable range, a rate of change of sensor data above a predetermined level, a requirement for calibration of a sensor, a temperature measurement outside a predetermined range, or any combination thereof.

The processed sensor data for the time period of disabled information output may be displayed substantially immediately upon processing.

The processed sensor data for the time period of disabled information output may be displayed only after waiting a predetermined period of time.

In another embodiment, an apparatus may include an interface configured to receive sensor data, a first memory configured to store the received sensor data, a processor coupled to the memory and configured to process the stored sensor data, a second memory coupled to the processor and configured to store the processed sensor data, and a display unit coupled to the second memory and configured to display the processed sensor data, wherein the processor is further configured to detect a condition unsuitable for calibration of a sensor for a predetermined time period, disable display of processed sensor data, determine a successful calibration of the sensor, retrieve one or more parameters associated with the successful calibration, process the sensor data during the time period of disabled display of sensor data with the one or more parameters associated with the successful calibration, and display the processed sensor data for the time period of disabled information output.

The sensor may be an analyte sensor.

The analyte sensor may be a glucose sensor.

The sensor data may correspond to analyte concentration data.

The analyte concentration data may include blood glucose concentration data.

Furthermore, the apparatus may be configured to process and display the sensor data substantially in real-time.

In one aspect, the condition unsuitable for calibration may include one or more of a failure mode of a sensor, sensor data outside a predetermined acceptable range, a rate of change of sensor data above a predetermined level, a requirement for calibration of a sensor, a temperature measurement outside a predetermined range, or any combination thereof.

The display unit may be configured to display the processed sensor data for the time period of disabled information output substantially immediately upon processing the sensor data.

The display unit may be configured to display the processed sensor data for the time period of disabled information output only after waiting a predetermined period of time.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present disclosure and that structures and methods within the scope of these claims and their equivalents be covered thereby.

What is claimed is:

1. A glucose monitoring system comprising:
   a glucose sensor, a portion of which is configured to be positioned under skin of the user, wherein the glucose sensor comprises at least two electrodes, and wherein the glucose sensor is configured to sample a biological fluid of the user to provide sensor data;
   a transmitter unit coupled to the glucose sensor, the transmitter unit comprising a power supply, a processor of the transmitter unit, memory of the transmitter unit, and a radio frequency transceiver of the transmitter unit, wherein the transmitter unit is configured to:
   receive the sensor data from the glucose sensor,
   process the sensor data using calibration data to provide processed sensor data, wherein the calibration data comprises data associated with a sensitivity of the glucose sensor, and wherein the processed sensor data is stored in the memory of the transmitter unit, and
   transmit the processed sensor data over a Bluetooth wireless communication link using the radio frequency transceiver of the transmitter unit; and
   a primary receiver unit comprising a processor of the primary receiver unit, memory of the primary receiver unit, a radio frequency transceiver of the primary receiver unit, an antenna, and a display, wherein the primary receiver unit is configured to:
   receive, using the antenna and the radio frequency transceiver of the primary receiver unit, the processed sensor data over the Bluetooth wireless communication link,
   output to the display of the primary receiver unit, a numerical value based on the processed sensor data, and
   output to the display of the primary receiver unit, a first line graph that is a continuous depiction of the processed sensor data over time,
   wherein the transmitter unit and at least a portion of the glucose sensor are disposed within a single integrated housing,
   wherein the glucose monitoring system is configured to detect an adverse condition, wherein the adverse condition comprises a signal error associated with the transmitter unit, wherein the adverse condition results in the primary receiver unit displaying a data gap such that the first line graph displayed on the primary receiver unit has an end corresponding to a time associated with a start of the adverse condition,
   wherein, during a time period corresponding to the adverse condition, processed sensor data is stored in the memory of the transmitter unit,
   wherein the primary receiver unit is configured to output to the display, after the adverse condition is corrected, processed sensor data for the time period corresponding to the adverse condition such that the data gap is backfilled, and
   wherein the processed sensor data for the time period corresponding to the adverse condition that is outputted to the display after the adverse condition is corrected comprises a second line graph having a first end corresponding to the time associated with the start of the adverse condition and a second end corresponding to a time associated with an end of the adverse condition.

2. The glucose monitoring system of claim 1, wherein the first line graph and the second line graph are outputted to a same graph comprising a first axis having a time unit of measurement and a second axis having a glucose concentration unit of measurement.

3. The glucose monitoring system of claim 2, wherein the primary receiver unit is further configured to display the second line graph immediately after correction of the adverse condition.

4. The glucose monitoring system of claim 2, wherein the primary receiver unit is further configured to wait a predetermined period of time after correction of the adverse condition before displaying the second line graph.

5. The glucose monitoring system of claim 1, wherein the at least two electrodes comprise a working electrode and a counter electrode.

6. The glucose monitoring system of claim 1, wherein the transmitter unit, the primary receiver unit, or both is further configured to store time information associated with the adverse condition.

7. The glucose monitoring system of claim 1, wherein the time period associated with the adverse condition comprises at least one hour.

8. The glucose monitoring system of claim 1, wherein the glucose monitoring system is further configured for periodic calibration, and wherein the calibration data is based at least in part on glucose reference data received after the portion of the glucose sensor has been positioned under the skin of the user.

9. The glucose monitoring system of claim 8, wherein the glucose monitoring system is further configured for calibration twelve hours after the portion of the glucose sensor has been positioned under the skin of the user.

10. The glucose monitoring system of claim 1, wherein the transmitter unit is configured to transition from a low-power mode to an operating mode, and wherein the transmitter unit consumes more power from the power supply in the operating mode than in the low-power mode.

11. The glucose monitoring system of claim 10, wherein the power supply of the transmitter unit is configured to provide power for about three months of continuous operation.

12. The glucose monitoring system of claim 1, further comprising a secondary receiver unit, wherein the secondary receiver unit is configured to receive processed sensor data.

13. The glucose monitoring system of claim 12, wherein the secondary receiver unit is configured to include a limited number of functions as compared with the primary receiver unit.

14. The glucose monitoring system of claim 13, wherein the secondary receiver unit is a watch.

15. The glucose monitoring system of claim 1, wherein the adverse condition further comprises a condition in which the primary receiver unit is outside a communication range of the transmitter unit.

16. A glucose monitoring system comprising:
a glucose sensor, a portion of which is configured to be positioned under skin of the user, wherein the glucose sensor comprises at least two electrodes, and wherein the glucose sensor is configured to sample a biological fluid of the user to provide sensor data;
a transmitter unit coupled to the glucose sensor, the transmitter unit comprising a power supply, a processor of the transmitter unit, memory of the transmitter unit, and a radio frequency transceiver of the transmitter unit, wherein the transmitter unit is configured to:
receive the sensor data from the glucose sensor,
process the sensor data using calibration data to provide processed sensor data, wherein the calibration data comprises data associated with a sensitivity of the glucose sensor, and wherein the processed sensor data is stored in the memory of the transmitter unit, and
transmit the processed sensor data over a Bluetooth wireless communication link using the radio frequency transceiver of the transmitter unit; and
a primary receiver unit comprising a processor of the primary receiver unit, memory of the primary receiver unit, a radio frequency transceiver of the primary receiver unit, an antenna, and a display, wherein the primary receiver unit is configured to:
receive, using the antenna and the radio frequency transceiver of the primary receiver unit, the processed sensor data over the Bluetooth wireless communication link,
output to the display of the primary receiver unit, a numerical value based on the processed sensor data, and
output to the display of the primary receiver unit, a first line graph that is a continuous depiction of the processed sensor data over time,
wherein the transmitter unit and at least a portion of the glucose sensor are disposed within a single integrated housing,
wherein the glucose monitoring system is configured to detect an adverse condition, wherein the adverse condition comprises a signal error associated with the primary receiver unit, wherein the adverse condition results in the primary receiver unit displaying a data gap such that the first line graph displayed on the primary receiver unit has an end corresponding to a time associated with a start of the adverse condition,
wherein, during a time period corresponding to the adverse condition, processed sensor data is stored in the memory of the transmitter unit,
wherein the primary receiver unit is configured to output to the display, after the adverse condition is corrected, processed sensor data for the time period corresponding to the adverse condition such that the data gap is backfilled, and
wherein the processed sensor data for the time period corresponding to the adverse condition that is outputted to the display after the adverse condition is corrected comprises a second line graph having a first end corresponding to the time associated with the start of the adverse condition and a second end corresponding to a time associated with an end of the adverse condition.

17. The glucose monitoring system of claim 16, wherein the primary receiver unit is further configured to display the second line graph immediately after correction of the adverse condition.

18. The glucose monitoring system of claim 16, wherein the primary receiver unit is further configured to wait a predetermined period of time after correction of the adverse condition before displaying the second line graph.

19. The glucose monitoring system of claim 16, further comprising a secondary receiver unit, wherein the secondary receiver unit is configured to receive processed sensor data, and wherein the secondary receiver unit is a watch.

20. The glucose monitoring system of claim 16, wherein the adverse condition further comprises a condition in which the primary receiver unit is outside a communication range of the transmitter unit.

21. The glucose monitoring system of claim 16, wherein the time period associated with the adverse condition comprises at least one hour.

22. A glucose monitoring system comprising:
a glucose sensor, a portion of which is configured to be positioned under skin of the user, wherein the glucose sensor comprises at least a working electrode and a counter electrode, wherein the glucose sensor is configured to sample a biological fluid of the user to provide sensor data;
a transmitter unit coupled to the glucose sensor, the transmitter unit comprising a power supply, a processor of the transmitter unit, memory of the transmitter unit, and a radio frequency transceiver of the transmitter unit, wherein the transmitter unit is configured to:
receive the sensor data from the glucose sensor and store the sensor data in the memory of the data processing and transmitter unit,
process the sensor data using calibration data to provide processed sensor data, wherein the calibration data comprises data associated with a sensitivity of the glucose sensor, and wherein the processed sensor data is stored in the memory of the transmitter unit, and
transmit the processed sensor data over a Bluetooth wireless communication link using the radio frequency transceiver of the transmitter unit; and
a primary receiver unit comprising a processor of the primary receiver unit, memory of the primary receiver unit, a radio frequency transceiver of the primary receiver unit, an antenna, and a display, wherein the primary receiver unit is configured to:
receive, using the antenna and the radio frequency transceiver of the primary receiver unit, the processed sensor data over the Bluetooth wireless communication link,
output to the display of the primary receiver unit, a numerical value based on the processed sensor data, and output to the display of the primary receiver unit, a first line graph that is a continuous depiction of the processed sensor data over time, wherein the transmitter unit and at least a portion of the glucose sensor are disposed within a single integrated housing, wherein the glucose monitoring system is configured to detect an adverse condition, wherein the adverse condition comprises one or more sensor data values being outside a predetermined range, wherein the adverse condition results in the primary receiver unit displaying a data gap such that the first line graph displayed on the primary receiver unit has an end corresponding to a time associated with a start of the adverse condition, wherein, during a time period corresponding to the adverse condition, sensor data is stored in the memory of the data processing and transmitter unit, wherein the primary receiver unit is configured to output to the display, after the adverse condition is corrected, processed sensor data for the time period corresponding to the adverse condition such that the data gap is backfilled, wherein the processed sensor data for the time period corresponding to the adverse condition that is outputted to the display after the adverse condition is corrected comprises a second line graph having a first end corresponding to the time associated with the start of the adverse condition and a second end corresponding to a time associated with an end of the adverse condition, and wherein the first line graph and the second line graph are outputted to a same graph comprising a first axis having a time unit of measurement and a second axis having a glucose concentration unit of measurement.

23. The glucose monitoring system of claim 22, wherein the primary receiver unit is further configured to display the second line graph immediately after correction of the adverse condition.

24. The glucose monitoring system of claim 22, wherein the primary receiver unit is further configured to wait a predetermined period of time after correction of the adverse condition before displaying the second line graph.

25. The glucose monitoring system of claim 22, wherein the transmitter unit and at least a portion of the glucose sensor are disposed within a single integrated housing.

26. The glucose monitoring system of claim 22, further comprising a secondary receiver unit, wherein the secondary receiver unit is configured to receive processed sensor data.

27. The glucose monitoring system of claim 26, wherein the secondary receiver unit is a watch.

28. The glucose monitoring system of claim 22, wherein the time period associated with the adverse condition comprises at least one hour.

* * * * *